(12) United States Patent
Rowland et al.

(10) Patent No.: US 8,563,489 B2
(45) Date of Patent: *Oct. 22, 2013

(54) ALKYLATED 1,3-BENZENEDIAMINE COMPOUNDS AND METHODS FOR PRODUCING SAME

(75) Inventors: Robert G. Rowland, Woodbridge, CT (US); Joseph F. Stieber, Prospect, CT (US); Clifford M. Pratt, Bethel, CT (US); Ronald D. Abbott, New Hartford, CT (US)

(73) Assignee: Chemtura Corporation, Middlebury, CT (US)

(*) Notice: Subject to any disclaimer, the term of this patent is extended or adjusted under 35 U.S.C. 154(b) by 410 days.

This patent is subject to a terminal disclaimer.

(21) Appl. No.: 12/212,131

(22) Filed: Sep. 17, 2008

(65) Prior Publication Data

US 2009/0156449 A1 Jun. 18, 2009

Related U.S. Application Data

(63) Continuation-in-part of application No. 12/001,951, filed on Dec. 12, 2007.

(51) Int. Cl.
*C10M 133/12* (2006.01)

(52) U.S. Cl.
USPC ............................................................. 508/557

(58) Field of Classification Search
None
See application file for complete search history.

(56) References Cited

U.S. PATENT DOCUMENTS

| | | | |
|---|---|---|---|
| 2,393,889 A | 1/1946 | Cook et al. | |
| 2,451,642 A | 10/1948 | Watson | |
| 2,718,501 A | 9/1955 | Harle | |
| 2,857,424 A | 10/1958 | Cox | |
| 2,883,362 A | 4/1959 | Rosenwald | |
| 3,087,936 A | 4/1963 | Suer | |
| 3,185,704 A | 5/1965 | Kahn et al. | |
| 3,211,793 A | 10/1965 | Roos | |
| 3,254,025 A | 5/1966 | Suer | |
| 3,304,285 A | 2/1967 | Cox | |
| 3,336,386 A | 8/1967 | Dovell et al. | |
| 3,402,201 A | 9/1968 | Schmerlling | |
| 3,442,808 A | 5/1969 | Traise et al. | |
| 3,629,330 A | 12/1971 | Brody et al. | |
| 3,632,511 A | 1/1972 | Liano | |
| T939,016 I4 * | 10/1975 | Douglas | 521/128 |
| 4,431,841 A | 2/1984 | Malz, Jr. et al. | |
| 4,487,759 A | 12/1984 | Nesbitt et al. | |
| 4,579,675 A | 4/1986 | Sawicki et al. | |
| 4,612,132 A | 9/1986 | Wollenberg et al. | |
| 4,663,064 A | 5/1987 | Nalesnik et al. | |
| 4,839,071 A | 6/1989 | Gutierrez et al. | |
| 4,839,072 A | 6/1989 | Gutierrez et al. | |
| 4,867,890 A | 9/1989 | Colclough et al. | |
| 4,868,054 A | 9/1989 | Kartheiser | |
| 4,966,721 A | 10/1990 | Farng et al. | |
| 5,026,495 A | 6/1991 | Emert et al. | |
| 5,041,668 A | 8/1991 | Nalepa et al. | |
| 5,085,788 A | 2/1992 | Emert et al. | |
| 5,207,939 A | 5/1993 | Farng et al. | |
| 5,259,906 A | 11/1993 | Poplanski et al. | |
| 5,312,461 A | 5/1994 | Farng et al. | |
| 5,328,622 A | 7/1994 | Emert et al. | |
| 5,334,321 A | 8/1994 | Harrison et al. | |
| 5,356,552 A | 10/1994 | Harrison et al. | |
| 5,407,591 A | 4/1995 | Emert et al. | |
| 5,711,767 A | 1/1998 | Gande et al. | |
| 5,716,912 A | 2/1998 | Harrison et al. | |
| 5,849,676 A | 12/1998 | Harrison et al. | |
| 5,861,363 A | 1/1999 | Willis, Jr. et al. | |
| 5,925,790 A | 7/1999 | Wheeler et al. | |
| 2006/0021159 A1 | 2/2006 | Sabelle et al. | |
| 2006/0052260 A1 | 3/2006 | Duyck et al. | |
| 2006/0128574 A1 | 6/2006 | Dong et al. | |
| 2006/0189824 A1 | 8/2006 | Kumar et al. | |
| 2007/0006855 A1 | 1/2007 | Malandro et al. | |
| 2009/0156441 A1 * | 6/2009 | Rowland et al. | 508/251 |

FOREIGN PATENT DOCUMENTS

| | | | |
|---|---|---|---|
| GB | 699349 | 11/1953 | |
| GB | 835826 | 5/1960 | |
| GB | 1296592 | 11/1972 | |
| JP | 59-020392 | 2/1984 | |
| WO | WO 2006/104528 A1 | 10/2006 | |
| WO | 2007/064528 A2 | 6/2007 | |
| WO | WO 2007/079367 A1 | 7/2007 | |
| WO | WO2007079365 | * 7/2007 | C08G 18/32 |

OTHER PUBLICATIONS

Kozaki et al. Tetrahedron Letters 39 (1998) 5979-5982.*
European Search Report for EP 08104794 mailed Nov. 24, 2008 (3 pages).
Partial European Search Report for EP 08104795 mailed Jan. 28, 2009 (7 pages).
Oberster, A.E. et al., 45 Can. J. Chem. 195-201 (1967).
Abstract of Makogon, A.N. et al., 12 Khemicheskaya Promyshlennost, Seriya: Metody Analiza Kontrolya Kachestva Produkstll v Khimicheskoi Promyshlennosti 18-21 (1980).
Dvolaitzky et al. "Stable N,N'-Di-tert-butyl-meta-phenylenebisnitroxides—Unexpected Ground State Singlets", XP002335877 (Jan. 1, 1992) Angew; Chem.Int.Ed.Engl. 31 (1992) No. 2. pp. 180-181.
Abdel-Magid, et al.. "Reductive Amination of Aldehydes and Ketones with Sodium Triacetoxyborohydride. Studies on Direct and Indirect Reductive Amination Procedures." J. Org. Chem. 61(1996): 3849-3862.

* cited by examiner

*Primary Examiner* — Clinton Brooks

(74) *Attorney, Agent, or Firm* — Joseph Suhadolnik; Chemtura Corporation

(57) ABSTRACT

An alkylated 1,3-benzenediamine compound used as a deposit-control lubricant additives for organic materials including lubricating oil, gasoline, and diesel fuels. The invention improves the oxidative stability of the lubricants and fuels by adding the alkylated 1,3-benzenediamine compound. The alkylated 1,3-benzenediamine compound is formed using a catalytic hydrogenation that alkylates the 4 and/or 6 position of the central aromatic ring.

3 Claims, No Drawings

ALKYLATED 1,3-BENZENEDIAMINE COMPOUNDS AND METHODS FOR PRODUCING SAME

CROSS REFERENCE TO RELATED APPLICATIONS

The present invention is a continuation-in-part of co-pending U.S. application Ser. No. 12/001,951, filed on Dec. 12, 2007, the entire contents and disclosure of which are hereby incorporated by reference.

FIELD OF THE INVENTION

The present invention relates to alkylated 1,3-benzenediamines, and more specifically alkylated $N^1,N^3$-dicycloalkyl-1,3-benzenediamines and methods for producing the same. Such alkylated 1,3-benzenediamines may be used, for example, as antioxidants, stabilizers, and antiozonants for lubricants, electronic chemicals, urethanes, crop protection, pharmaceuticals, dyes and toners.

BACKGROUND OF THE INVENTION

Lubricants, such as those used in a variety of machinery, are susceptible to oxidative deterioration during storage, transportation, and usage, particularly when such lubricants are exposed to high temperatures and iron catalytic environments, which greatly promote their oxidation. This oxidation, if not controlled, contributes to the formation of corrosive acidic products, sludge, varnishes, resins, and other oil-insoluble products and may lead to a loss of designated physical and tribological properties of the lubricants. These oxidation products may lead to the formation of harmful deposits on critical engine parts, such as the pistons, piston liners, valves, and valve lifters. It is therefore a common practice to include deposit-control and antioxidant additives in lubricants to prevent, at least to some extent, oxidation, so as to extend the useful life of the lubricants.

Lubricant compositions containing various secondary diarylamines as antioxidants are widely known in the art. The use of 1,4-benzenediamines is also known, as exemplified in U.S. Pat. Nos. 2,718,501, 2,883,362, 3,211,793, 3,304,285, and 5,711,767, U.S. Publication Nos. 2006/0128574, 2006/0189824, and 2007/0006855, GB1296592, and GB0835826 and JP59020392, the entire contents and disclosures of which are incorporated herein by reference. 1,4-benzenediamines have more commonly been employed as motor fuel stabilizers and antiozonants and antioxidants for rubber. There have been few reported 1,3-benzenediamines described suitable for use as antioxidants.

U.S. Pat. No. 2,451,642 discloses metaphenylenediamine, $N^1,N^3$-dimethyl-meta-phenylenediamine, and lauryl-meta-phenylenediamine as useful antioxidants for lubricating oil compositions for use in environments where iron-catalyzed oxidation reaction can take place. N,N'-dimethyl-ortho-phenylenediamine, N,N'-dicyclohexyl-para-phenylenediamine, and various di- and tetra-n-alkyl-para-phenylenediamines are similarly disclosed.

U.S. Pat. No. 2,857,424 discloses the preparation of oxalic acid salts of fuel stabilizing N,N'-dialkyl-para-phenylenediamines as a way of rendering the additives less toxic. The preparation of the oxalate salt of N,N'-dicyclohexyl-para-phenylenediamine is disclosed. The preparation of the oxalate salts of other unspecified dicycloalkyl ortho-, meta-, and para-phenylenediamines is contemplated.

Oberster, A. E. et al., 45 CAN. J. CHEM. 195-201 (1967), prepared 39 novel phenylenediamines as part of a program to find antiozonants for rubber that are not sensitizers or dermatotoxic. In some compounds the N'-phenylenediamine nitrogen was variously fused into a pyrrolidine, piperidine, hexamethyleneimine (homopiperidine), morpholine, or 2,6-dimethylmorpholine ring. In each case the N-cyclohexyl compound was prepared.

U.S. Pat. No. 3,402,201 discloses N,N'-dicyclooctyl-p-phenylenediamine as a stabilizer for organic materials, particularly rubber, and exemplifies its use as a gasoline inhibitor. The similar use of N,N'-dicyclooctyl-o- and m-phenylenediamines is contemplated.

Makogon, A. N. et al., 12 KHEMICHESKAYA PROMYSHLENNOST, SERIYA: METODY ANALIZA I KONTROLYA KACHESTVA PRODUKTSII V KHIMICHESKOI PROMYSHLENNOSTI 18-21 (1980), describe the characterization of N,N'-dialkyl-para-phenylenediamines reaction products obtained by the catalytic alkylation of 4-aminodiphenylamine with $C_7$-$C_9$ alcohols.

U.S. Pat. No. 4,487,759 discloses the use of certain tertiary phenylene diamines of the structure:

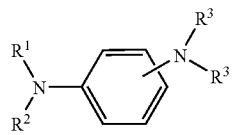

In particular, N,N',N'-trialkyl-N-phenyl-para-phenylenediamines (e.g., N,N'-didecyl-N'-octyl-N-phenyl-para-phenylenediamine) is used as light stabilizers for unsaturated insect pheromones that are contained in a micro-encapsulation delivery system.

U.S. Pat. Nos. 5,207,939 and 5,312,461 disclose certain Mannich base reaction products of mono- or dialkyl-phenylenediamines, an aldehyde or ketone, and a hindered phenol, which can be used in an antioxidant amount in lubricating oils, greases, and fuel compositions. Specifically the phenylenediamines compounds have the formula:

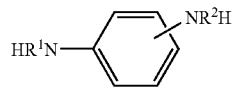

Japan Patent No. 59-020,392 discloses a lubricant composition comprising N,N'-di-sec-butyl-para-phenylenediamine for pressure forming of oil tanks. The lubricant composition also contains hindered phenolic antioxidant.

The foregoing disclosures are incorporated by reference.

While phenylenediamines are known to act effectively as antioxidants, these compounds have been found to be disadvantageous commercially, since the presence of such compounds, when used in amounts conventionally used to provide antioxidancy, displayed adverse effects on piston deposit and varnish control and also displayed aggressiveness toward fluoroelastomeric engine seal materials. These adverse effects are particularly apparent with phenylenediamine compounds having higher nitrogen contents (compounds having relatively small hydrocarbyl substituents). Recent lubricating oil specifications for passenger car diesel engine lubricating oil (PCDO) set by original equipment manufacturers (OEMs)

have required reduced levels of lubricant phosphorus (e.g., less than 800 ppm). To date, lubricating oil specifications for heavy duty diesel (HDD) engines have not limited phosphorus content, although the next generation of lubricant specifications (e.g., API CJ-4) is expected to do so. Expected limits on phosphorus content (such as to 1200 ppm or less), and reductions in the allowable amounts of sulfated ash (SASH) and sulfur will limit the amount of zinc dialkyldithiophosphate (ZDDP), one of the most cost-effective antiwear/antioxidant compounds, that a lubricant formulator can use.

BRIEF SUMMARY OF THE INVENTION

In a first aspect of the present invention, there is provided a compound of structure (I) having the general formula:

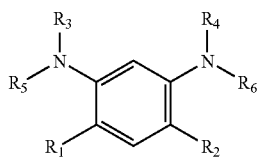
(I)

wherein $R_1$ and $R_2$ are independently selected from the group consisting of $C_1$-$C_{20}$ alkyl, $C_2$-$C_{20}$ alkenyl, $C_4$-$C_{20}$ cycloalkyl, $C_5$-$C_{20}$ aryl, $C_5$-$C_{20}$ heterocyclo and hydrogen, provided that at least one of $R_1$ and $R_2$ is not hydrogen; wherein $R_3$ and $R_4$ are independently selected from the group consisting of $C_1$-$C_{20}$ alkyl, $C_2$-$C_{20}$ alkenyl, $C_4$-$C_{20}$ cycloalkyl, $C_5$-$C_{20}$ aryl, and $C_5$-$C_{20}$ heterocyclo; and wherein $R_5$ and $R_6$ are independently selected from the group consisting of hydrogen, $C_1$-$C_{20}$ alkyl, $C_2$-$C_{20}$ alkenyl, $C_4$-$C_{20}$ cycloalkyl, $C_5$-$C_{20}$ aryl, and $C_5$-$C_{20}$ heterocyclo.

In a second aspect of the present invention, there is provided a process for alkylating a 1,3-benzenediamine compound comprising providing a carbonyl compound selected from the group consisting of an aldehyde having the general formula:

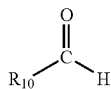

and a ketone having the general formula:

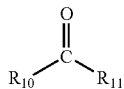

wherein $R_{10}$ and $R_{11}$ are independently selected from the group consisting of $C_1$-$C_{20}$ alkyl, $C_2$-$C_{20}$ alkenyl, $C_4$-$C_{20}$ cycloalkyl, $C_5$-$C_{20}$ aryl, $C_5$-$C_{20}$ heterocyclo and a ring compound formed by fusing $R_{10}$ and $R_{11}$ to form a $C_4$-$C_{20}$ cycloalkyl, $C_5$-$C_{20}$ aryl, or $C_5$-$C_{20}$ heterocyclo; and reacting the carbonyl compound with the 1,3-benzenediamine compound in the presence of hydrogen and a hydrogenation catalyst to form a structure (I) having the general formula:

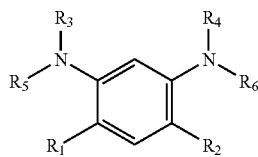
(I)

wherein $R_1$ and $R_2$ are independently selected from the group consisting of $C_1$-$C_{20}$ alkyl, $C_2$-$C_{20}$ alkenyl, $C_4$-$C_{20}$ cycloalkyl, $C_5$-$C_{20}$ aryl, $C_5$-$C_{20}$ heterocyclo and hydrogen, provided that at least one of $R_1$ and $R_2$ is not hydrogen; wherein $R_3$ and $R_4$ are independently selected from the group consisting of $C_1$-$C_{20}$ alkyl, $C_2$-$C_{20}$ alkenyl, $C_4$-$C_{20}$ cycloalkyl, $C_5$-$C_{20}$ aryl, and $C_5$-$C_{20}$ heterocyclo; and wherein $R_5$ and $R_6$ are independently selected from the group consisting of hydrogen, $C_1$-$C_{20}$ alkyl, $C_2$-$C_{20}$ alkenyl, $C_4$-$C_{20}$ cycloalkyl, $C_5$-$C_{20}$ aryl, and $C_5$-$C_{20}$ heterocylo.

In a third aspect of the present invention, there is provided a process for alkylating a 1,3-benzenediamine compound comprising providing a first carbonyl compound selected from the group consisting of an aldehyde having the general formula:

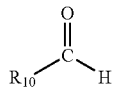

and a ketone having the general formula:

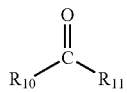

wherein $R_{10}$ and $R_{11}$ are independently selected from the group consisting of $C_1$-$C_{20}$ alkyl, $C_2$-$C_{20}$ alkenyl, $C_4$-$C_{20}$ cycloalkyl, $C_5$-$C_{20}$ aryl, $C_5$-$C_{20}$ heterocyclo and a ring compound formed by fusing $R_{10}$ and $R_{11}$ to form a $C_4$-$C_{20}$ cycloalkyl, $C_5$-$C_{20}$ aryl, or $C_5$-$C_{20}$ heterocyclo; providing a second carbonyl compound selected from an aldehyde having the general formula:

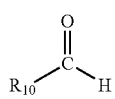

and a ketone having the general formula:

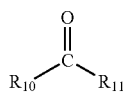

wherein $R_{10}$ and $R_{11}$ are independently selected from the group consisting of hydrogen, $C_1$-$C_{20}$ alkyl, $C_2$-$C_{20}$ alkenyl, $C_4$-$C_{20}$ cycloalkyl, $C_5$-$C_{20}$ aryl, and $C_5$-$C_{20}$ heterocyclo, wherein the first carbonyl compound is different than the second carbonyl compound; reacting the first carbonyl compound with a 1,3-benzenediamine compound in the presence of hydrogen and a hydrogenation catalyst to form an intermediate having a general formula selected from the group consisting of:

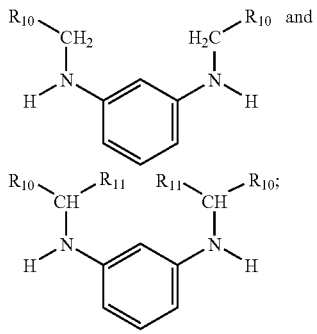

and reacting the second carbonyl compound with the intermediate compound in the presence of hydrogen and a hydrogenation catalyst to form the alkylated 1,3-benzenediamine compound having a general formula selected from the group consisting of:

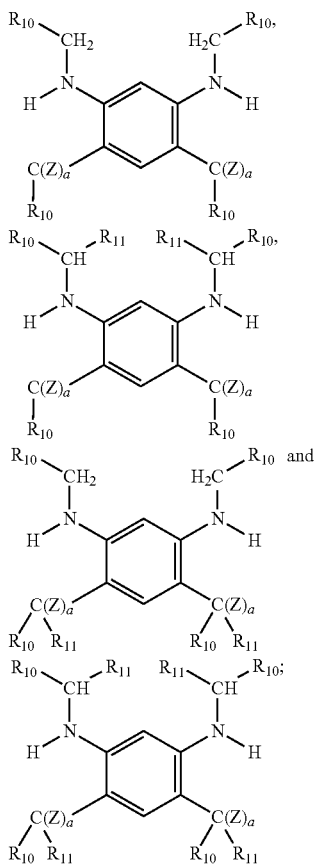

wherein Z=H, and a=0, 1, or 2.

In a fourth aspect of the present invention, there is provided a lubricating oil composition, comprising: at least one base stock of lubricating viscosity in an amount from 80 wt % to 99.99 wt %, based on the total mass of the composition; and an antioxidant in an amount from 0.01 wt % to 6 wt % based on the total mass of the composition, the antioxidant comprising at least one compound having a structure (I) having the general formula:

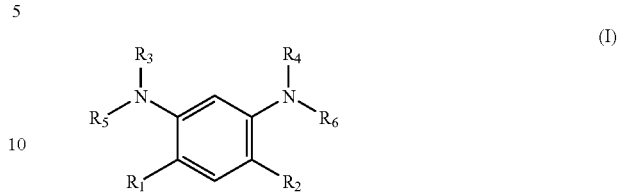

wherein $R_1$ and $R_2$ are independently selected from the group consisting of $C_1$-$C_{20}$ alkyl, $C_2$-$C_{20}$ alkenyl, $C_4$-$C_{20}$ cycloalkyl, $C_5$-$C_{20}$ aryl, $C_5$-$C_{20}$ heterocyclo and hydrogen, provided that at least one of $R_1$ and $R_2$ is not hydrogen; wherein $R_3$ and $R_4$ are independently selected from the group consisting of $C_1$-$C_{20}$ alkyl, $C_2$-$C_{20}$ alkenyl, $C_4$-$C_{20}$ cycloalkyl, $C_5$-$C_{20}$ aryl, and $C_5$-$C_{20}$ heterocyclo; and wherein $R_5$ and $R_6$ are independently selected from the group consisting of hydrogen, $C_1$-$C_{20}$ alkyl, $C_2$-$C_{20}$ alkenyl, $C_4$-$C_{20}$ cycloalkyl, $C_5$-$C_{20}$ aryl, and $C_5$-$C_{20}$ heterocyclo.

In a fifth aspect of the present invention, there is provided a $N^1,N^3$-dialkyl-4,6-dialkyl-1,3-benzenediamine. In one embodiment the $N^1,N^3$-dialkyl-4,6-dialkyl-1,3-benzenediamine comprises a $N^1,N^3$-dicyclohexyl-4,6-dialkyl-1,3-benzenediamine, such as $N^1,N^3$-dicyclohexyl-4,6-diisobutyl-1,3-benzenediamine.

In a sixth aspect of the present invention, there is provided a lubricating oil composition, comprising at least one base stock of lubricating viscosity in an amount from 80 wt % to 99.99 wt %, based on the total mass of the composition; and a $N^1,N^3$-dicycloalkyl-4,6-dialkyl-1,3-benzenediamine in an amount from 0.01 wt % to 6 wt % based on the total mass of the composition.

DETAILED DESCRIPTION OF THE PREFERRED EMBODIMENTS

Introduction

The present invention is generally related to alkylated 1,3-benzenediamines and processes for alkylating 1,3-benzenediamines. In one embodiment, 1,3-benzenediamine is alkylated with an aldehyde or ketone in the presence of a reducing agent to form secondary amine groups. Optionally, the 1,3-benzenediamine is reacted with an aldehyde or ketone using catalytic hydrogenation. In either case, the nitrogens of the 1,3-benzenediamines are selectively alkylated rather than the benzene component thereof. The resulting $N^1,N^3$-dialkylated-1,3-benzenediamine product is then reacted with an aldehyde or ketone using catalytic hydrogenation. Although this second alkylation step would similarly be expected to alkylate the amine groups of the $N^1,N^3$-dialkylated-1,3-benzenediamine, it has surprisingly and unexpectedly been discovered that, unlike the first alkylation step, the second alkylation step selectively alkylates the central aromatic ring of the alkylated 1,3-benzenediamine. Thus, the process preferentially forms $N^1,N^3$-dialkyated-4,6-dialkylated-1,3-benzenediamines rather than $N^1,N^1,N^3,N^3$-alkyated-1,3-benzenediamines.

Novel Alkylated Benzene Diamines

In various embodiments, as indicated above, the present invention is directed to novel alkylated 1,3-benzenediamine compounds. In one embodiment, for example, the invention is to an alkylated 1,3-benzenediamine having the formula:

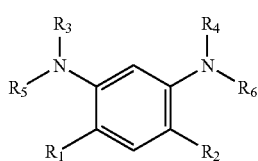
(I)

wherein $R_1$ and $R_2$ are independently selected from the group consisting of linear or branched $C_1$-$C_{20}$ alkyl, linear or branched $C_2$-$C_{20}$ alkenyl, substituted or unsubstituted $C_4$-$C_{20}$ cycloalkyl, substituted or unsubstituted $C_5$-$C_{20}$ aryl, substituted or unsubstituted $C_5$-$C_{20}$ heterocyclo and hydrogen, provided that at least one of $R_1$ and $R_2$ is not hydrogen; $R_3$ and $R_4$ are independently selected from the group consisting of linear or branched $C_1$-$C_{20}$ alkyl, linear or branched $C_2$-$C_{20}$ alkenyl, substituted or unsubstituted $C_4$-$C_{20}$ cycloalkyl, substituted or unsubstituted $C_5$-$C_{20}$ aryl, substituted or unsubstituted $C_5$-$C_{20}$ heterocyclo; and $R_5$ and $R_6$ are independently selected from the group consisting of hydrogen, linear or branched $C_1$-$C_{20}$ alkyl, linear or branched $C_2$-$C_{20}$ alkenyl, substituted or unsubstituted $C_4$-$C_{20}$ cycloalkyl, substituted or unsubstituted $C_5$-$C_{20}$ aryl, and substituted or unsubstituted $C_5$-$C_{20}$ heterocyclo. In one embodiment, $R_5$ and $R_6$ are preferably hydrogen.

The cycloalkyl, aryl, and heterocyclo may be substituted with a linear or branched $C_1$-$C_{12}$ alkyl groups. In one embodiment, the cycloalkyl, aryl, and heterocyclo may be substituted with halogens, linear or branched $C_1$-$C_{20}$ alkyl, and linear or branched $C_2$-$C_{20}$ alkenyl. The halogens may be selected from the group consisting of F, Cl, Br, and I.

In one embodiment, any of the alkyl, alkenyl, cycloalkyl, aryl or heterocyclo groups may comprise one or more heteroatoms selected from the group consisting of N, O, and S.

In one embodiment, $R_1$ and $R_2$ are the same substituent, such as a branched or unbranched alkyl group having 3 to 6 carbons or alkyl substituted 5 to 8 carbon aryl group. Similarly, $R_3$ and $R_4$ may be the same substituent, such as cyclohexyl or 1,3-dimethylbutyl, and $R_5$ and $R_6$ may be the same substituent, such as hydrogen.

Representative examples of alkyl groups for use herein for $R_1$, $R_2$, $R_3$, $R_4$, $R_5$, and $R_6$ include, for example, a straight or branched hydrocarbon chain radical containing from 1 to 20 carbon atoms, e.g., methyl, ethyl, n-propyl, 1-methylethyl (isopropyl), n-butyl, isobutyl, sec-butyl, 1,3-dimethylbutyl, 1,4-dimethylpentyl, n-pentyl, isopentyl, 1,5-dimethylhexyl, and hexyl, etc., mixtures and isomers thereof, and the like.

Representative examples of alkenyl groups for use herein for $R_1$, $R_2$, $R_3$, $R_4$, $R_5$, and $R_6$ include, for example, a straight or branched hydrocarbon chain radical containing from 2 to 20 carbon atoms, e.g., ethylidene, propenyl, 2-methyl-propenyl, butenyl, pentenyl, hexenyl, etc., mixtures and isomers thereof, and the like. Such alkenyl groups may also include allyl and methylallyl. The alkenyl group may have one or more double bonds and may include dialkenyl groups, trialkenyl groups, tetraalkenyl groups, etc.

Representative examples of cycloalkyl groups for use herein for $R_1$, $R_2$, $R_3$, $R_4$, $R_5$, and $R_6$ include, for example, substituted or unsubstituted rings containing from 4 to 20 carbon atoms, e.g., cyclobutyl, cyclopentyl, cyclohexyl, n-methyl-cyclohexyl, n-dimethyl-cyclohexyl, n-ethyl-cyclohexyl, cycloheptyl, cyclooctyl, etc., mixtures and isomers thereof, and the like.

Representative examples of aryl groups for use herein for $R_1$, $R_2$, $R_3$, $R_4$, $R_5$, and $R_6$ include, for example, substituted or unsubstituted aromatic rings containing from 5 to 20 carbon atoms, e.g., phenyl, n-methylphenyl, n-dimethylphenyl, n-ethylphenyl, benzyl, naphthyl, tetrahydronapthyl, indenyl, biphenyl, etc., mixtures and isomers thereof, and the like.

Representative examples of heterocyclo groups for use herein for $R_1$, $R_2$, $R_3$, $R_4$, $R_5$, and $R_6$ include, for example, substituted or unsubstituted rings containing from 5 to 20 carbon atoms, e.g., furfuryl and tetrahydrofurfuryl.

Preferably, the alkylated 1,3-benzenediamine has, or has on average, a nitrogen content from about 2 to about 15 weight percent (wt %), e.g., from about 5 to about 11 wt %, or from about 5.5 to about 10.5 wt %, based on the total weight of the alkylated 1,3-benzenediamine.

In one embodiment, the alkylated 1,3-benzenediamine of the present invention has the general formula:

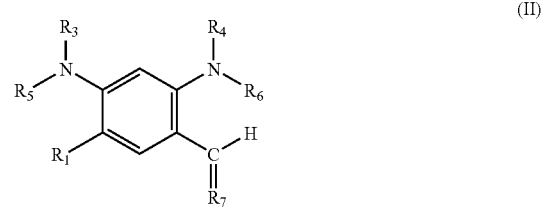
(II)

wherein $R_1$, $R_3$, $R_4$, $R_5$, and $R_6$ are defined above, and $R_7$ is selected from the group consisting of $C_1$-$C_{20}$ alkyl, $C_2$-$C_{20}$ alkenyl, $C_4$-$C_{20}$ cycloalkyl, $C_5$-$C_{20}$ aryl, and $C_5$-$C_{20}$ heterocyclo.

In one embodiment, the alkylated 1,3-benzenediamine of the present invention has the general formula selected from the group consisting of:

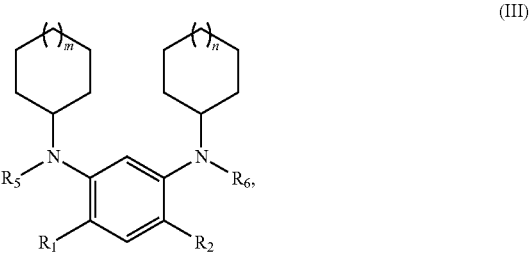
(III)

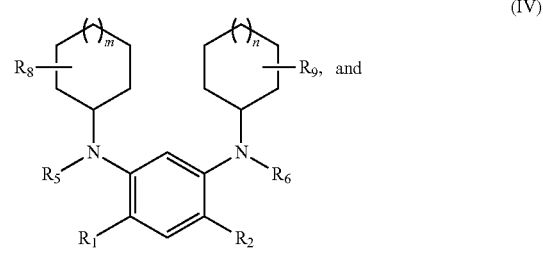
(IV)

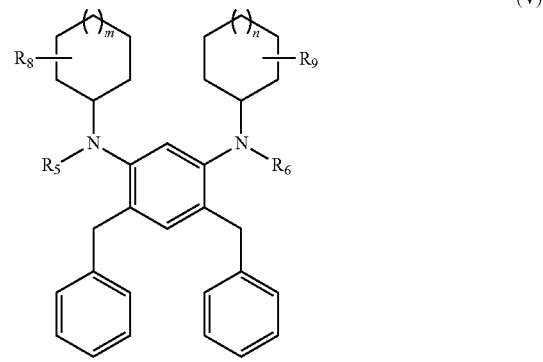
(V)

wherein m and n are independently 0, 1, 2 or 3, $R_1$ and $R_2$ are independently selected from the group consisting of linear or branched $C_1$-$C_{20}$ alkyl, linear or branched $C_2$-$C_{20}$ alkenyl, substituted or unsubstituted $C_4$-$C_{20}$ cycloalkyl, substituted or unsubstituted $C_5$-$C_{20}$ aryl, substituted or unsubstituted $C_5$-$C_{20}$ heterocyclo and hydrogen, provided that at least one of $R_1$ and $R_2$ is not hydrogen; and $R_5$, $R_6$, $R_8$, and $R_9$ are independently selected from the group consisting of hydrogen, halogen, linear or branched $C_1$-$C_{20}$ alkyl, linear or branched $C_2$-$C_{20}$ alkenyl, substituted or unsubstituted $C_4$-$C_{20}$ cycloalkyl, substituted or unsubstituted $C_5$-$C_{20}$ aryl, and substituted or unsubstituted $C_5$-$C_{20}$ heterocyclo. In one embodiment, $R_1$ or $R_2$ are both not hydrogen. Either or both $R_8$, and $R_9$ may be a halogen.

In another embodiment, the alkylated 1,3-benzenediamine of the present invention has the general formula selected from the group consisting of:

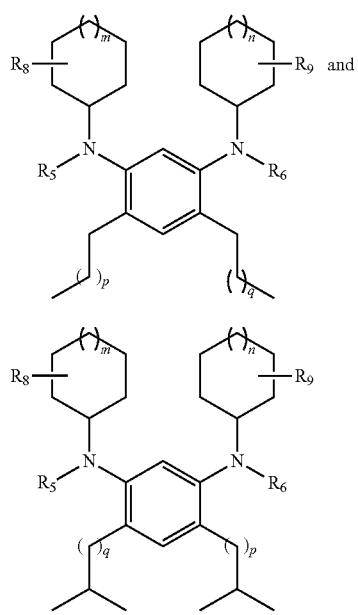

(VI)

(VII)

wherein m and n are independently integers of 0, 1, 2 or 3, p and q are independently integers from 0 to 18, and $R_5$, $R_6$, $R_8$, and $R_9$ are independently selected from the group consisting of hydrogen, halogen, linear or branched $C_1$-$C_{20}$ alkyl, linear or branched $C_2$-$C_{20}$ alkenyl, substituted or unsubstituted $C_4$-$C_{20}$ cycloalkyl, substituted or unsubstituted $C_5$-$C_{20}$ aryl, and substituted or unsubstituted $C_5$-$C_{20}$ heterocyclo. In one embodiment, $R_1$ or $R_2$ are both not hydrogen. Either or both $R_8$, and $R_9$ may be a halogen.

In another embodiment, the alkylated 1,3-benzenediamine of the present invention has the general formula selected from the group consisting of:

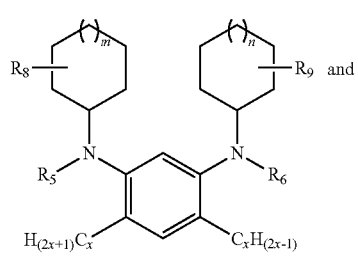

(VIII)

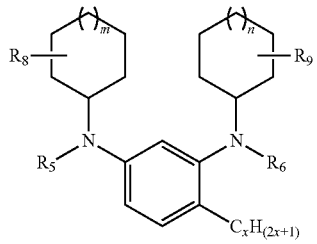

(IX)

wherein m and n are independently 0, 1, 2 or 3, x is an integer from 2 to 18, and $R_5$, $R_6$, $R_8$, and $R_9$ are independently selected from the group consisting of hydrogen, halogen, linear or branched $C_1$-$C_{20}$ alkyl, linear or branched $C_2$-$C_{20}$ alkenyl, substituted or unsubstituted $C_4$-$C_{20}$ cycloalkyl, substituted or unsubstituted $C_5$-$C_{20}$ aryl, and substituted or unsubstituted $C_5$-$C_{20}$ heterocyclo. In one embodiment, $R_1$ or $R_2$ are both not hydrogen. Either or both $R_8$, and $R_9$ may be a halogen.

In another embodiment, the alkylated 1,3-benzenediamine of the present invention has the general formula selected from the group consisting of:

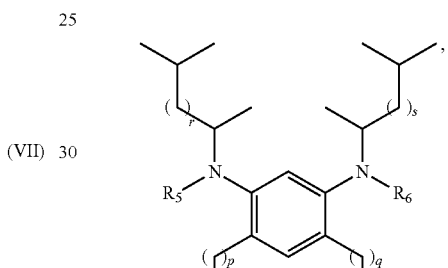

(X)

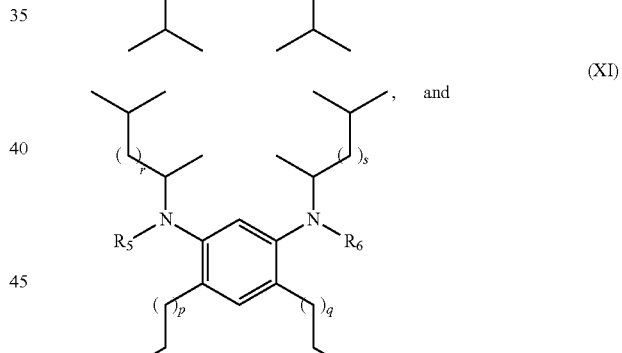

(XI)

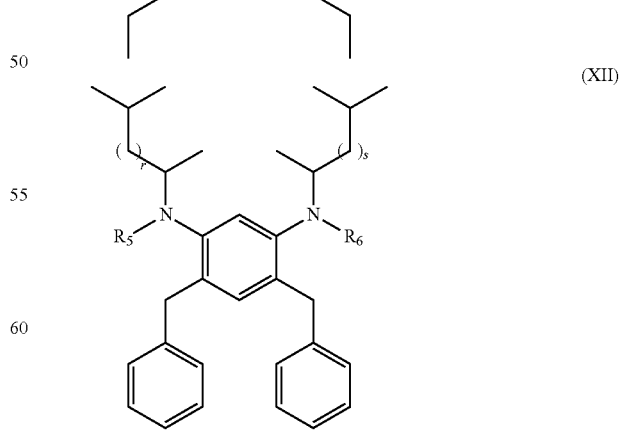

(XII)

wherein p and q are independently integers from 0 to 18, r and s are independently integers of 1 or 2, and $R_5$ and $R_6$ are independently selected from the group consisting of hydrogen, halogen, linear or branched $C_1$-$C_{20}$ alkyl, linear or branched $C_2$-$C_{20}$ alkenyl, substituted or unsubstituted $C_4$-$C_{20}$ cycloalkyl, substituted or unsubstituted $C_5$-$C_{20}$ aryl, and substituted or unsubstituted $C_5$-$C_{20}$ heterocyclo.

It should be understood that the alkylated 1,3-benzenediamine of the present invention may have the general formula selected from the group consisting of formulas (III)-(XII).

In a preferred embodiment, the alkylated 1,3-benzenediamine of the present invention has the general formula:

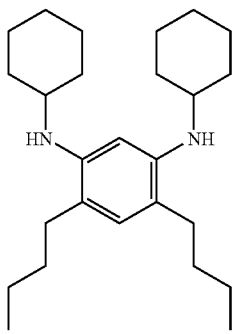

(XIII)

In a preferred embodiment, the alkylated 1,3-benzenediamine of the present invention has the general formula:

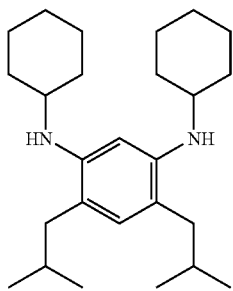

(XIV)

In a preferred embodiment, the alkylated 1,3-benzenediamine of the present invention has the general formula:

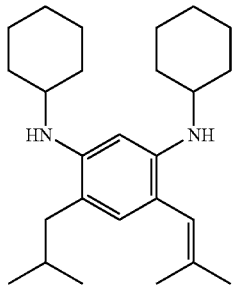

(XV)

In a preferred embodiment, the alkylated 1,3-benzenediamine of the present invention has the general formula:

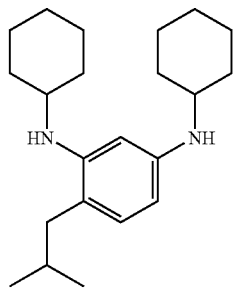

(XVI)

In a preferred embodiment, the alkylated 1,3-benzenediamine of the present invention has the general formula:

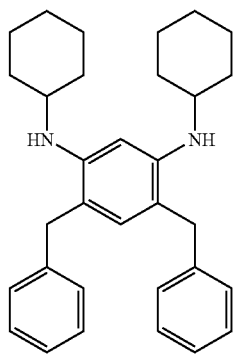

(XVII)

In a preferred embodiment, the alkylated 1,3-benzenediamine of the present invention has the general formula:

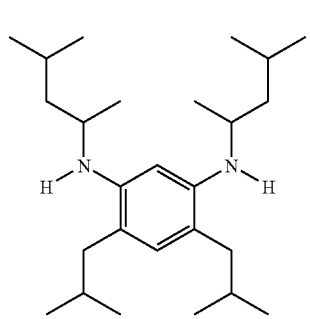

(XVIII)

In a preferred embodiment, the alkylated 1,3-benzenediamine of the present invention has the general formula:

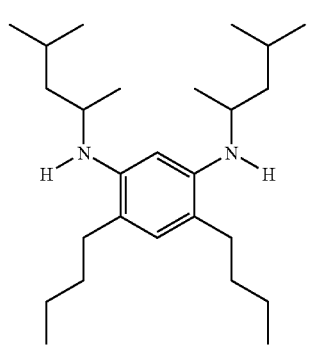

(XIX)

Alkylated 1,3-benzenediamines of the present invention may include $N^1,N^3$-dialkyl-4,6-dialkyl-1,3-benzenediamine, such as a $N^1,N^3$-dicyclohexyl-4,6-dialkyl-1,3-benzenediamine or $N^1,N^3$-dicyclohexyl-4,6-diisobutyl-1,3-benzenediamine. The 4,6-dialkyl substituent is selected from the group consisting of $C_1$-$C_{20}$ alkyl, $C_2$-$C_{20}$ alkenyl, $C_4$-$C_{20}$ cycloalkyl, $C_5$-$C_{20}$ aryl, and $C_5$-$C_{20}$ heterocyclo.

Exemplary alkylated 1,3-benzenediamines of the present invention include, but are not limited to: $N^1,N^3$-dicyclohexyl-4-methyl-1,3-benzenediamine; $N^1,N^3$-dicyclohexyl-4-ethyl-1,3-benzenediamine; $N^1,N^3$-dicyclohexyl-4-propyl-1,3-benzenediamine; $N^1,N^3$-dicyclohexyl-4-butyl-1,3-benzenediamine; $N^1,N^3$-dicyclohexyl-4-isobutyl-1,3-benzenediamine; $N^1,N^3$-dicyclohexyl-4-heptyl-1,3-benzenediamine; $N^1,N^3$-dicyclohexyl-4-ethenyl-1,3-benzenediamine; $N^1,N^3$-dicyclohexyl-4-propenyl-1,3-benzenediamine; $N^1,N^3$-dicyclohexyl-4-isobutenyl-1,3-benzenediamine; $N^1,N^3$-dicyclohexyl-4-butenyl-1,3-benzenediamine; $N^1,N^3$-dicyclohexyl-4-heptenyl-1,3-benzenediamine; $N^1,N^3$-dicyclohexyl-4-benzyl-1,3-benzenediamine; $N^1,N^3$-dicyclohexyl-4-furfuryl-1,3-benzenediamine; $N^1,N^3$-dicyclohexyl-4,6-dimethyl-1,3-benzenediamine; $N^1,N^3$-dicyclohexyl-4,6-diethyl-1,3-benzenediamine; $N^1,N^3$-dicyclohexyl-4,6-dipropyl-1,3-benzenediamine; $N^1,N^3$-dicyclohexyl-4,6-dibutyl-1,3-benzenediamine; $N^1,N^3$-dicyclohexyl-4,6-diisobutyl-1,3-benzenediamine; $N^1,N^3$-dicyclohexyl-4-isobutenyl-6-isobutyl-1,3-benzenediamine; $N^1,N^3$-dicyclohexyl-4,6-diheptyl-1,3-benzenediamine; $N^1,N^3$-dicyclohexyl-4,6-diethenyl-1,3-benzenediamine; $N^1,N^3$-dicyclohexyl-4,6-dipropenyl-1,3-benzenediamine; $N^1,N^3$-dicyclohexyl-4,6-diisobutenyl-1,3-benzenediamine; $N^1,N^3$-dicyclohexyl-4,6-dibutenyl-1,3-benzenediamine; $N^1,N^3$-dicyclohexyl-4,6-diheptenyl-1,3-benzenediamine; $N^1,N^3$-dicyclohexyl-4,6-dibenzyl-1,3-benzenediamine; $N^1,N^3$-dicyclohexyl-4,6-difurfuryl-1,3-benzenediamine; $N^1,N^3$-dicyclopentyl-4-methyl-1,3-benzenediamine; $N^1,N^3$-dicyclopentyl-4-ethyl-1,3-benzenediamine; $N^1,N^3$-dicyclopentyl-4-propyl-1,3-benzenediamine; $N^1,N^3$-dicyclopentyl-4-butyl-1,3-benzenediamine; $N^1,N^3$-dicyclopentyl-4-isobutyl-1,3-benzenediamine; $N^1,N^3$-dicyclopentyl-4-heptyl-1,3-benzenediamine; $N^1,N^3$-dicyclopentyl-4-ethenyl-1,3-benzenediamine; $N^1,N^3$-dicyclopentyl-4-propenyl-1,3-benzenediamine; $N^1,N^3$-dicyclopentyl-4-isobutenyl-1,3-benzenediamine; $N^1,N^3$-dicyclopentyl-4-butenyl-1,3-benzenediamine; $N^1,N^3$-dicyclopentyl-4-heptenyl-1,3-benzenediamine; $N^1,N^3$-dicyclopentyl-4-benzyl-1,3-benzenediamine; $N^1,N^3$-dicyclopentyl-4-furfuryl-1,3-benzenediamine; $N^1,N^3$-dicyclopentyl-4,6-dimethyl-1,3-benzenediamine; $N^1,N^3$-dicyclopentyl-4,6-diethyl-1,3-benzenediamine; $N^1,N^3$-dicyclopentyl-4,6-dipropyl-1,3-benzenediamine; $N^1,N^3$-dicyclopentyl-4,6-dibutyl-1,3-benzenediamine; $N^1,N^3$-dicyclopentyl-4,6-diisobutyl-1,3-benzenediamine; $N^1,N^3$-dicyclopentyl-4-isobutenyl-6-isobutyl-1,3-benzenediamine; $N^1,N^3$-dicyclopentyl-4,6-diheptyl-1,3-benzenediamine; $N^1,N^3$-dicyclopentyl-4,6-diethenyl-1,3-benzenediamine; $N^1,N^3$-dicyclopentyl-4,6-dipropenyl-1,3-benzenediamine; $N^1,N^3$-dicyclopentyl-4,6-diisobutenyl-1,3-benzenediamine; $N^1,N^3$-dicyclopentyl-4,6-dibutenyl-1,3-benzenediamine; $N^1,N^3$-dicyclopentyl-4,6-diheptenyl-1,3-benzenediamine; $N^1,N^3$-dicyclopentyl-4,6-dibenzyl-1,3-benzenediamine; $N^1,N^3$-dicyclopentyl-4,6-difurfuryl-1,3-benzenediamine; $N^1,N^3$-(1,3-dimethylbutyl)-4-methyl-1,3-benzenediamine; $N^1,N^3$-(1,3-dimethylbutyl)-4-ethyl-1,3-benzenediamine; $N^1,N^3$-(1,3-dimethylbutyl)-4-propyl-1,3-benzenediamine; $N^1,N^3$-(1,3-dimethylbutyl)-4-butyl-1,3-benzenediamine; $N^1,N^3$-(1,3-dimethylbutyl)-4-isobutyl-1,3-benzenediamine; $N^1,N^3$-(1,3-dimethylbutyl)-4-heptyl-1,3-benzenediamine; $N^1,N^3$-(1,3-dimethylbutyl)-4-ethenyl-1,3-benzenediamine; $N^1,N^3$-(1,3-dimethylbutyl)-4-propenyl-1,3-benzenediamine; $N^1,N^3$-(1,3-dimethylbutyl)-4-isobutenyl-1,3-benzenediamine; $N^1,N^3$-(1,3-dimethylbutyl)-4-butenyl-1,3-benzenediamine; $N^1,N^3$-(1,3-dimethylbutyl)-4-heptenyl-1,3-benzenediamine; $N^1,N^3$-(1,3-dimethylbutyl)-4-benzyl-1,3-benzenediamine; $N^1,N^3$-(1,3-dimethylbutyl)-4-furfuryl-1,3-benzenediamine; $N^1,N^3$-(1,3-dimethylbutyl)-4,6-dimethyl-1,3-benzenediamine; $N^1,N^3$-(1,3-dimethylbutyl)-4,6-diethyl-1,3-benzenediamine; $N^1,N^3$-(1,3-dimethylbutyl)-4,6-dipropyl-1,3-benzenediamine; $N^1,N^3$-(1,3-dimethylbutyl)-4,6-dibutyl-1,3-benzenediamine; $N^1,N^3$-(1,3-dimethylbutyl)-4,6-diisobutyl-1,3-benzenediamine; $N^1,N^3$-(1,3-dimethylbutyl)-4-isobutenyl-6-isobutyl-1,3-benzenediamine; $N^1,N^3$-(1,3-dimethylbutyl)-4,6-diheptyl-1,3-benzenediamine; $N^1,N^3$-(1,3-dimethylbutyl)-4,6-diethenyl-1,3-benzenediamine; $N^1,N^3$-(1,3-dimethylbutyl)-4,6-dipropenyl-1,3-benzenediamine; $N^1,N^3$-(1,3-dimethylbutyl)-4,6-diisobutenyl-1,3-benzenediamine; $N^1,N^3$-(1,3-dimethylbutyl)-4,6-dibutenyl-1,3-benzenediamine; $N^1,N^3$-(1,3-dimethylbutyl)-4,6-diheptenyl-1,3-benzenediamine; $N^1,N^3$-(1,3-dimethylbutyl)-4,6-dibenzyl-1,3-benzenediamine; and $N^1,N^3$-(1,3-dimethylbutyl)-4,6-difurfuryl-1,3-benzenediamine; $N^1,N^3$-(1,3-dimethylbutyl)-4-methyl-1,3-benzenediamine; $N^1,N^3$-(1,3-dimethylbutyl)-4-ethyl-1,3-benzenediamine; $N^1,N^3$-(1,3-dimethylbutyl)-4-propyl-1,3-benzenediamine; $N^1,N^3$-(1,3-dimethylbutyl)-4-butyl-1,3-benzenediamine; $N^1,N^3$-(1,3-dimethylbutyl)-4-isobutyl-1,3-benzenediamine; $N^1,N^3$-(1,3-dimethylbutyl)-4-heptyl-1,3-benzenediamine; $N^1,N^3$-(1,3-dimethylbutyl)-4-ethenyl-1,3-benzenediamine; $N^1,N^3$-(1,3-dimethylbutyl)-4-propenyl-1,3-benzenediamine; $N^1,N^3$-(1,3-dimethylbutyl)-4-isobutenyl-1,3-benzenediamine; $N^1,N^3$-(1,3-dimethylbutyl)-4-butenyl-1,3-benzenediamine; $N^1,N^3$-(1,3-dimethylbutyl)-4-heptenyl-1,3-benzenediamine; $N^1,N^3$-(1,3-dimethylbutyl)-4-benzyl-1,3-benzenediamine; $N^1,N^3$-(1,3-dimethylbutyl)-4-furfuryl-1,3-benzenediamine; $N^1,N^3$-(1,3-dimethylbutyl)-4,6-dimethyl-1,3-benzenediamine; $N^1,N^3$-(1,3-dimethylbutyl)-4,6-diethyl-1,3-benzenediamine; $N^1,N^3$-(1,3-dimethylbutyl)-4,6-dipropyl-1,3-benzenediamine; $N^1,N^3$-(1,3-dimethylbutyl)-4,6-dibutyl-1,3-benzenediamine; $N^1,N^3$-(1,3-dimethylbutyl)-4,6-diisobutyl-1,3-benzenediamine; $N^1,N^3$-(1,3-dimethylbutyl)-4-isobutenyl-6-isobutyl-1,3-benzenediamine; $N^1,N^3$-(1,3-dimethylbutyl)-4,6-diheptyl-1,3-benzenediamine; $N^1,N^3$-(1,3-dimethylbutyl)-4,6-diethenyl-1,3-benzenediamine; $N^1,N^3$-(1,3-dimethylbutyl)-4,6-dipropenyl-1,3-benzenediamine; $N^1,N^3$-(1,3-dimethylbutyl)-4,6-diisobutenyl-1,3-benzenediamine; $N^1,N^3$-(1,3-dimethylbutyl)-4,6-dibutenyl-1,3-benzenediamine; $N^1,N^3$-(1,3-dimethylbutyl)-4,6-diheptenyl-1,3-benzenediamine; $N^1,N^3$-(1,3-dimethylbutyl)-4,6-dibenzyl-1,3-benzenediamine; and $N^1,N^3$-(1,3-dimethylbutyl)-4,6-difurfuryl-1,3-benzenediamine.

In one embodiment the invention is to a composition comprising a mixture of two or more alkylated 1,3-benzenediamines selected from the structures and compounds identified above. Such mixtures may comprise a weight ratio of two different alkylated 1,3-benzenediamines of, for example, from 5:4 to 4:1, e.g., from 5:3 to 3:1 or about 2:1. In an exemplary embodiment, the mixture comprises $N^1,N^3$-dicyclohexyl-4,6-diisobutyl-1,3-benzenediamine and $N^1,N^3$-dicyclohexyl-4-isobutenyl-6-isobutyl-1,3-benzenediamine in a weight ratio from 5:4 to 4:1, e.g., from 5:3 to 3:1 or about 2:1.

Processes for Forming Alkylated 1,3-Benzenediamines

The present invention also generally relates to processes for forming alkylated 1,3-benzenediamines. In one embodiment, the process comprises alkylating an N,N'-dialkylated-1,3-benzenediamine. The alkylating step preferably comprises reacting the N,N'-dialkylated-1,3-benzenediamine with an carbonyl compound, i.e. aldehyde or ketone, and hydrogen under catalytic hydrogenation conditions effective to selectively alkylate the benzene ring of the N,N'-dialkylated-1,3-benzenediamine, preferably at the 4 and/or 6 positions thereof.

As used herein, the term alkylating or alkylation refers to adding a substituent that mainly comprises a hydrocarbon structure. This includes, but is not limited to, adding an alkyl group, alkenyl group, cycloalkyl group, aryl group or heterocyclo group. In one embodiment alkylating may refer to adding a cycloalkyl or aryl group that is substituted with an alkyl group and/or contains one or more halogens or heteroatoms.

The process for forming 1,3-benzenediamine is well known and may involve nitration of benzene with nitric acid followed by hydrogenation. In one embodiment, the invention is to a multi-step alkylation process that begins with 1,3-benzenediamine. In this embodiment, the 1,3-benzenediamine is alkylated in a first alkylation step to form the N,N'-dialkylated-1,3-benzenediamine by reducing each amine. The resulting N,N'-dialkylated-1,3-benzenediamine is then alkylated in a second alkylation step by reacting the N,N'-dialkylated-1,3-benzenediamine with an carbonyl compound using catalytic hydrogenation to selectively alkylate the benzene ring of the N,N'-dialkylated-1,3-benzenediamine, preferably at the 4 and/or 6 positions thereof, to form the final N,N'-dialkylated-4-alkylated-1,3-benzenediamine product, or N,N'-dialkylated-4,6-dialkylated-1,3-benzenediamine product.

In the first alkylation step, the alkylated 1,3-benzenediamine intermediate may be created using either a reductive alkylation or alkylating through a catalytic hydrogenation. Processes for reductively alkylating 1,3-benzenediamine with an carbonyl compound are disclosed in Abdel-Majid, A. F. et al., 61 J. ORG. CHEM. 3849-62 (1996), the entirety of which is incorporated herein by reference. Those skilled in the art will recognize that adjustments in stoichiometry, reaction time, and reaction temperature may be required to achieve the desired reaction with varying starting materials.

Suitable reducing agents for such reductive alkylation processes include, for example, sodium triacetoxyborohydride (STAB-H), sodium-cyanoborohydride, borane-pyridine, $Ti(OiPr)_4/NaBH_3CN$, $Zn/AcOH$, $NaBH$ $Mg(ClO_4)_2$, $Zn(BH_4)_2/ZnCl_2$ and borohydride exchange resins. In one embodiment the first alkylation step employs STAB-H.

In such reductive alkylation processes, the carbonyl compound may comprise an aldehyde having the general formula:

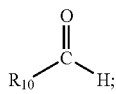

or ketone having the general formula:

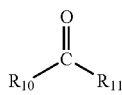

wherein $R_{10}$ and $R_{11}$ are independently selected from the group consisting of linear or branched $C_1$-$C_{20}$ alkyl, linear or branched $C_2$-$C_{20}$ alkenyl, $C_4$-$C_{20}$ cycloalkyl (e.g., cyclobutyl, cyclopentyl, cyclohexyl, cycloheptyl, cyclooctyl), $C_5$-$C_{20}$ aryl, and $C_5$-$C_{20}$ heterocyclo. Optionally, $R_{10}$ and $R_{11}$ are fused to form a ring compound such as $C_4$-$C_{20}$ cycloalkyl, $C_5$-$C_{20}$ aryl, or $C_5$-$C_{20}$ heterocyclo. Exemplary ring compound include cyclobutyl, cyclopentyl, cyclohexyl, cycloheptyl, and cyclooctyl. In one embodiment, the ketone may be methylisobutylketone (MIBK) methylisoamylketone (MIAK), cyclopentanone, or cyclohexanone.

In some embodiments, the reductive alkylation process may use one or more solvents. Suitable solvents include, for example, xylenes, 1-2-dichloroethane, tetrahydrofuran, and acetonitrile. Solvents may be removed from the reaction mixture, for example, by rotary evaporation or other conventional separation techniques.

The mixture temperature and duration may vary widely depending on the compounds used. For example, the reducing agent may be added to the mixture of 1,3-benzenediamine and aldehyde/ketone at a temperature from 25° C. to 80° C., e.g., from 40° C. to 50° C. or about 35° C., for 1 hour to 10 hours, e.g., 2 to 8 hours or 3 to 5 hours.

In another embodiment, the first alkylation step involves a catalytic hydrogenation in which 1,3-benzenediamine is reacted with an carbonyl compound, i.e. aldehyde or ketone, in the presence of hydrogen and a hydrogenation catalyst instead of the above-described reductive alkylation process. In this embodiment, 1,3-benzenediamine and the carbonyl compound are reacted in the presence of hydrogen and a hydrogenation catalyst. Similar to the reductive alkylation process, 1,3-benzenediamines that are alkylated on the nitrogen atoms (i.e., having secondary amines) may be synthesized.

In such catalytic hydrogenation, the carbonyl compound may comprise an aldehyde having the general formula:

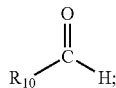

or ketone having the general formula:

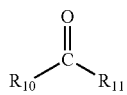

wherein $R_{10}$ and $R_{11}$ are independently selected from the group consisting of linear or branched $C_1$-$C_{20}$ alkyl, linear or branched $C_2$-$C_{20}$ alkenyl, $C_4$-$C_{20}$ cycloalkyl (e.g., cyclobutyl, cyclopentyl, cyclohexyl, cycloheptyl, cyclooctyl), $C_5$-$C_{20}$ aryl, and $C_5$-$C_{20}$ heterocyclo. Optionally, $R_{10}$ and $R_{11}$ are fused to form a ring compound of a $C_4$-$C_{20}$ cycloalkyl, $C_5$-$C_{20}$ aryl, or $C_5$-$C_{20}$ heterocyclo, e.g., cyclobutyl, cyclopentyl, cyclohexyl, cycloheptyl, cyclooctyl. In one embodiment, the ketone may be MIBK, MIAK, cyclopentanone, or cyclohexanone.

Suitable hydrogenation catalysts include platinum, palladium, rhodium, ruthenium, osmium, iridium or nickel catalysts. In one embodiment, the catalyst comprises a supported catalyst. The catalyst support may comprise, for example, carbon, alumina, silica, aluminosilicates, etc.

The catalytic hydrogenation preferably is carried out in a pressurized reactor. In one embodiment the reactor is pressured with 100-30,000 kilopascals (KPa) of hydrogen, e.g., 500-10,000 KPa or 3,500-5,000 KPa.

The temperature of the catalytic hydrogenation preferably ranges from 20° C. to 300° C., e.g., from 80° C. to 250° C. or from 120° C. to 220° C.

As indicated above, in the first alkylation step, the aldehyde or ketone selectively adds to the primary amine groups of the 1,3-benzenediamine and forms a secondary amine intermediate compound. It would be expected that continued alkylation of the intermediate, whether by reductive alkylation or by hydrogenation, would similarly selectively add at the nitrogen positions of the N,N'-dialkylated-1,3-benzenediamines to form tertiary amines.

It has now surprisingly and unexpectedly been discovered, however, that catalytic hydrogenation of N,N'-dialkyl-1,3-benzenediamine intermediate with an carbonyl compound, i.e. aldehyde or ketone, results in selective alkylation of the benzene group rather than alkylation on the amine groups, as shown below in the comparison synthesis. In particular, the alkylating is specific to the 4 and/or the 6 positions of the central aromatic group.

Conventional Synthesis A

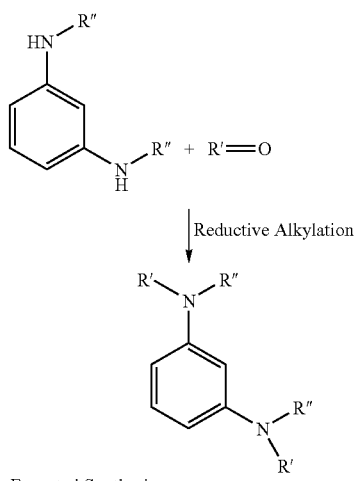

Reductive Alkylation

Expected Synthesis

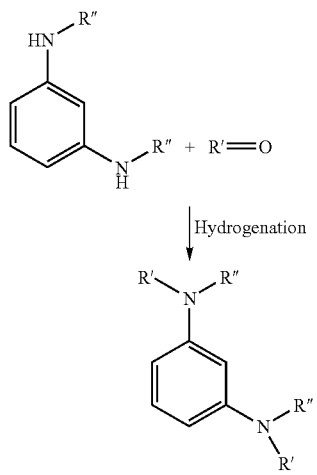

Hydrogenation

Embodiments of Present Invention

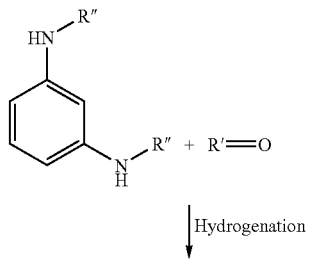

Hydrogenation

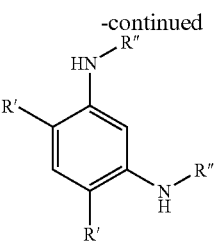

R' and R" represent any suitable substituent defined throughout this application.

Suitable carbonyl compounds for the catalytic hydrogenation of the N,N'-dialkyl-1,3-benzenediamine intermediate include aldehyde and ketones having the following structures:

aldehyde having the general formula:

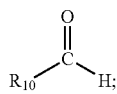

and ketone having the general formula:

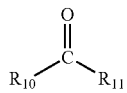

wherein $R_{10}$ and $R_{11}$ are independently selected from the group consisting of linear or branched $C_1$-$C_{20}$ alkyl, linear or branched $C_2$-$C_{20}$ alkenyl, $C_4$-$C_{20}$ cycloalkyl (e.g., cyclobutyl, cyclopentyl, cyclohexyl, cycloheptyl, cyclooctyl), $C_5$-$C_{20}$ aryl, and $C_5$-$C_{20}$ heterocyclo. Optionally, $R_{10}$ and $R_{11}$ are fused to form a ring compound, e.g., cyclobutyl, cyclopentyl, cyclohexyl, cycloheptyl, cyclooctyl.

The molar ratios of aldehyde or ketone to N,N'-dialkyl-1,3-benzenediamine intermediate may be from 5:1 to 1:5, e.g., from 3:1 to 1:3, or from 2:1 to 1:2.

In such catalytic hydrogenation, suitable hydrogenation catalysts include platinum, palladium, rhodium, ruthenium, osmium, iridium or nickel catalysts. In one embodiment, the catalyst comprises a supported catalyst. The catalyst support may comprise, for example, carbon, alumina, silica, aluminosilicates, etc.

The catalytic hydrogenation of the intermediate is preferably carried out in a pressurized reactor, which preferably has a pressure greater than 220 KPa, e.g., greater than 375 KPa or greater than 650 KPa. In terms of ranges, the reactor optionally is pressured at from 100-30,000 KPa of hydrogen, e.g., 500-10,000 KPa or 3,500-5,000 KPa.

The temperature of the catalytic hydrogenation preferably ranges from 20° C. to 300° C., e.g., from 80° C. to 250° C. or from 120° C. to 220° C. In one embodiment, the hydrogen to alkylate the central aromatic component of the intermediate may be carried at a higher temperature than the catalytic hydrogen to alkylate the primary amines. The higher temperature may be greater by an amount of from 10° C. to 100° C., e.g. from 25° C. to 75° C. or from 40° C. to 60° C.

In one embodiment, the reaction of carbonyl compounds with 1,3-benzenediamine involves two separate catalytic hydrogenation process. Such a process may comprise providing a first and second carbonyl compounds from the aldehyde and ketone formulas defined above, wherein the first carbonyl compound is different than the second carbonyl compound. In one embodiment, the first carbonyl compound may be a ketone, such a MIBK, MIAK, cyclopentanone, or cyclohexanone, and the second carbonyl compound may be an aldehyde, such as isobutyraldehyde or butyraldehyde. The first carbonyl compound is reacted with 1,3-benzenediamine compound under the catalytic hydrogenation conditions defined above to form an intermediate selected from the group consisting of:

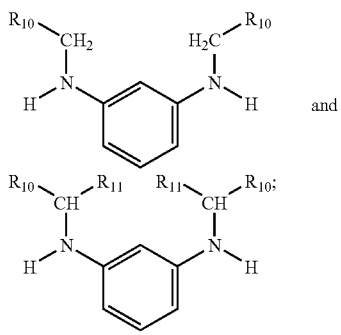

wherein $R_{10}$ and $R_{11}$ are defined above. As shown the intermediate comprises two secondary amines. Next, the second carbonyl compound is reacted with the intermediate under the catalytic hydrogenation conditions defined above to form the alkylated 1,3-benzenediamine compound having a general formula selected from the group consisting of:

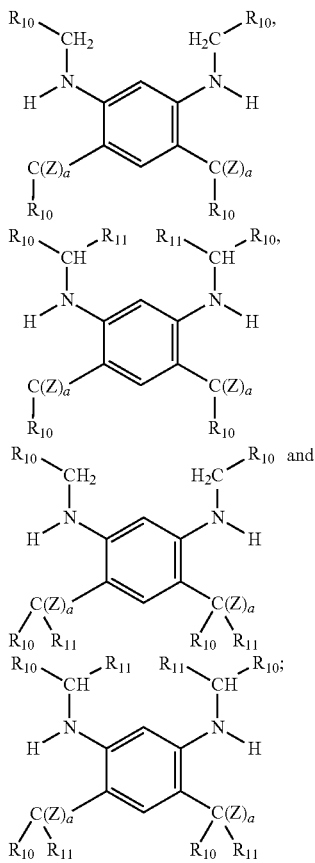

wherein $R_{10}$ and $R_{11}$ are defined above, Z=H, and a=0, 1, or 2. It should be understood that when a is 0 or 1 there may be a multiple bond between C and the respective R group.

In some embodiments, the process of the invention selectively alkylates solely at the 4 position rather than at both the 4 and 6 positions of the benzene group. Selective alkylation at the 4 position may be favored, for example, by decreasing the amount of aldehyde or ketone that is available to react with the N,N'-dialkyl-1,3-benzenediamine. For example, molar ratios of aldehyde or ketone to N,N'-dialkyl-1,3-benzenediamine less than 2:1, e.g., less than 1.5:1 or less than 1.2:1, may favor monoalkylation over dialkylation. In terms of ranges, molar ratios of aldehyde or ketone to N,N'-dialkyl-1,3-benzenediamine may be from 2:1 to 1:2, e.g., from 1.5:1 to 3:4, or from 1.2:1 to 5:6. Lower reaction temperatures and shorter reaction times, e.g., less than 3, less than 2 or less than 1 hour, may also favor monoalkylation.

In one such embodiment, N,N'-dialkyl-4-methyl-1,3-benzenediamine may be catalytically hydrogenated using with a carbonyl compound described above. The alkylation selectively occurs at the 6 position.

In some embodiments, the processes of the invention may form double bonds in the alkyl group that is added to the N,N'-dialkylated-1,3-benzenediamine. The formation of unsaturated alkyl groups may be favored, for example, by decreasing the partial pressure of hydrogen that is available to react and/or by decreasing the reaction time or temperature of the reaction vessel. The specific catalyst employed also may impact saturation.

Applications

The compositions of the present invention may be incorporated in a variety products, for example, to improve oxidative stability, and/or inhibit degradation or deposit formation. In a preferred embodiment, one or more of the alkylated-1,3-benzenediamine compositions of the invention may be incorporated into a fluid that otherwise would be subject to oxidative degradation. Thus, in one embodiment, the invention is to a fluid, e.g., lubricating fluid, comprising a base stock and a stabilizing amount of at least one of the alkylated-1,3-benzenediamine compositions of the present invention. Preferably, the fluid comprises the alkylated-1,3-benzenediamine in an amount sufficient to stabilize the fluid against the formation of deposits, relative to the same composition without the alkylated-1,3-benzenediamine.

In one embodiment, the invention is to a fluid, e.g., a lubricating oil composition, comprising at least one base stock, e.g., a base stock of lubricating viscosity, in an amount from 45 to 99.99 wt %, e.g., from 80 to 99.95 wt % or from 90 to 99 wt %, based on the total weight of the base stock and the alkylated 1,3-benzenediamine. The fluid also comprises one or more of the alkylated 1,3-benzenediamine compounds of the present invention in an amount from 0.01 to 6 wt %, e.g., from 0.05 to 4 wt %; or from 1 to 3 wt %, based on the total weight of the base stock and the alkylated 1,3-benzenediamine. Of course, other additives may also be included in the fluid, as described below. In one exemplary embodiment the base stock is present in an amount from 80 to 99.99 wt % and a compound in an amount from 0.01 to 6 wt %, wherein the compound has the formula:

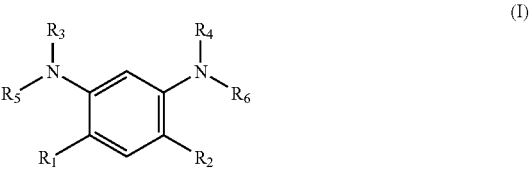

(I)

where each $R_1$, $R_2$, $R_3$, $R_4$, $R_5$ and $R_6$ are defined above.

In another exemplary embodiment, the invention is to a fluid, e.g., a lubricating oil composition, comprising a base stock and $N^1,N^3$-dicycloalkyl-4,6-dialkyl-1,3-benzenediamine. The base stock preferably is present in the fluid in an amount from 80 to 99.99 wt %, based on the total weight of the base stock and the $N^1,N^3$-dicycloalkyl-4,6-dialkyl-1,3-benzenediamine. The $N^1,N^3$-dicycloalkyl-4,6-dialkyl-1,3-benzenediamine preferably is present in the fluid in an amount from 0.01 to 6 wt %, based on the total weight of the base stock and the $N^1,N^3$-dicycloalkyl-4,6-dialkyl-1,3-benzenediamine.

In such embodiments, the lubricating oil composition has a sufficient amount of the alkylated 1,3-benzenediamine to stabilize the fluid against the formation of deposits. For example, the Mid-High Temperature Thermo-Oxidation Engine Oil Simulation Test (MHT-TEOST) indicates that such lubricating oil compositions may form from 1 to 70 mg, e.g., from 5 to 55 mg, or from 5 to 35 mg of deposits. Deposits of greater than 70 mg generally reflect an undesirably high level of deposit formation, while values less than 55 mg are generally deemed acceptable for most applications. Optionally, the fluids, e.g., lubricating oil compositions, of various embodiments of the invention form less than 50 mg of deposits, e.g., less than 30 mg of deposits, or less than 20 mg of deposits, as determined by the above-referenced MHT-TEOST.

Suitable base stocks for the lubricating viscosity compositions are selected from the group consisting of engine oils, transmission fluids, hydraulic fluids, gear oils, marine cylinder oils, compressor oils, refrigeration lubricants, aviation turbine oils, gas turbine oils, and mixtures thereof.

The compounds of the present invention improve the oxidative stability of organic materials, which are subject to oxidative, thermal, and/or light-induced degradation. These organic materials can be natural or synthetic. These organic materials can include "functional fluids," lubricating oils, greases, and fuels, as well as automatic and manual transmission fluids, power steering fluid, hydraulic fluids, gas turbine oils, compressor lubricants, automotive and industrial gear lubricants, and heat transfer oils. Lubricating oil compositions useful in the practice of the present invention comprise a major amount of oil of lubricating viscosity and a minor amount of at least one benzenediamine compound having one or more cycloalkyl substituents on each nitrogen atom.

Oils of lubricating viscosity useful in the context of the present invention can be selected from natural lubricating oils, synthetic lubricating oils, and mixtures thereof. The lubricating oil can range in viscosity from light distillate mineral oils to heavy lubricating oils, such as gasoline engine oils, mineral lubricating oils, and heavy duty diesel oils. Generally, the viscosity of the oil ranges from about 2 centistokes to about 40 centistokes, especially from about 4 centistokes to about 20 centistokes, as measured at 100° C.

The diesel fuel is a petroleum-based fuel oil, especially a middle distillate fuel oil. Such distillate fuel oils generally boil within the range of from 110° C. to 500° C., e.g., 150° C. to 400° C. The fuel oil may comprise atmospheric distillate or vacuum distillate, cracked gas oil, or a blend in any proportion of straight run and thermally and/or refinery streams such as catalytically cracked and hydro-cracked distillates.

Other examples of diesel fuels include Fischer-Tropsch fuels. Fischer-Tropsch fuels, also known as FT fuels, include those described as gas-to-liquid (GTL) fuels, biomass-to-liquid (BTL) fuels and coal conversion fuels. To make such fuels, syngas ($CO+H_2$) is first generated and then converted to normal paraffins by a Fischer-Tropsch process. The normal paraffins can then be modified by processes such as catalytic cracking/reforming or isomerization, hydrocracking and hydroisomerization to yield a variety of hydrocarbons such as iso-paraffins, cyclo-paraffins and aromatic compounds. The resulting FT fuel can be used as such or in combination with other fuel components and fuel types. Also suitable are diesel fuels derived from plant or animal sources. These can be used alone or in combination with other types of fuel.

Preferably, the diesel fuel has a sulfur content of at most 0.05% by weight, more preferably of at most 0.035% by weight, especially of at most 0.015%. Fuels with even lower levels of sulfur are also suitable, such as fuels with less than 50 ppm sulfur by weight, preferably less than 20 ppm, for example, 10 ppm or less.

Oils and fats derived from plant or animal materials are increasingly finding application as fuels and, in particular, as partial or complete replacements for petroleum derived middle distillate fuels such as diesel. Commonly, such fuels are known as "biofuels" or "biodiesels." Biofuels may be derived from many sources. Among the most common are the alkyl, often methyl, esters of fatty acids extracted from plants, such as rapeseed, sunflower, and the like. These types of fuel are often referred to as FAME (fatty acid methyl esters).

Natural oils include animal oils and vegetable oils (e.g., lard oil, castor oil); liquid petroleum oils and hydrorefined, solvent-treated or acid-treated mineral oils of the paraffinic, naphthenic, and mixed paraffinic-naphthenic types. Oils of lubricating viscosity derived from coal or shale also serve as useful base oils. Other examples of oils and fats derived from animal or vegetable material are rapeseed oil, coriander oil, soya bean oil, cottonseed oil, sunflower oil, castor oil, olive oil, peanut oil, maize oil, almond oil, palm kernel oil, coconut oil, mustard seed oil, jatropha oil, beef tallow, and fish oils. Further examples include oils derived from corn, jute, sesame, shea nut, ground nut, and linseed oil, and may be derived therefrom by methods known in the art. Rapeseed oil, which is a mixture of fatty acids partially esterified with glycerol, is available in large quantities and can be obtained in a simple way by pressing from rapeseed. Recycled oils such as used kitchen oils are also suitable.

Useful examples of alkyl esters of fatty acids can include commercial mixtures of the ethyl, propyl, butyl and especially methyl esters of fatty acids with 12 to 22 carbon atoms. For example, lauric acid, myristic acid, palmitic acid, palmitoleic acid, stearic acid, oleic acid, elaidic acid, petroselic acid, ricinoleic acid, elaeostearic acid, linoleic acid, linolenic acid, eicosanoic acid, gadoleic acid, docosanoic acid, or erucic acid are useful and have an iodine number from 50 to 150, especially 90 to 125. Mixtures with particularly advantageous properties are those which contain mainly, i.e., at least 50 wt. %, methyl esters of fatty acids with 16 to 22 carbon atoms and 1, 2, or 3 double bonds. The preferred lower alkyl esters of fatty acids are the methyl esters of oleic acid, linoleic acid, linolenic acid, and erucic acid.

Commercial mixtures of the stated kind are obtained for example by cleavage and esterification of animal and vegetable fats and oils by their transesterification with lower aliphatic alcohols. For production of alkyl esters of fatty acids, it is advantageous to start from fats and oils which contain low levels of saturated acids, less than 20%, and which have an iodine number of less than 130. Blends of the following esters or oils are suitable, e.g., rapeseed, sunflower, coriander, castor, soya bean, peanut, cotton seed, beef tallow, and the like. Alkyl esters of fatty acids based on a new variety of rapeseed oil, the fatty acid component of which comprises more than 80 wt. % unsaturated fatty acids with 18 carbon atoms, are preferred.

Particularly preferred are oils capable of being utilized as biofuels. Biofuels, i.e., fuels derived from animal or vegetable material, are believed to be less damaging to the environment on combustion and are obtained from a renewable source. It has been reported that on combustion less carbon dioxide is formed by the equivalent quantity of petroleum distillate fuel, e.g., diesel fuel, and very little sulfur dioxide is formed. Certain derivatives of vegetable oil, e.g., those obtained by saponification and re-esterification with a monohydric alkyl alcohol, can be used as a substitute for diesel fuel.

Preferred biofuels are vegetable oil derivatives, of which particularly preferred biofuels are alkyl ester derivatives of rapeseed oil, cottonseed oil, soya bean oil, sunflower oil, olive oil, or palm oil, rapeseed oil methyl ester being especially preferred, either alone or in admixture with other vegetable oil derivatives, e.g., mixtures in any proportion of rapeseed oil methyl ester and palm oil methyl ester.

At present, biofuels are most commonly used in combination with petroleum-derived oils. The present invention is applicable to mixtures of biofuel and petroleum-derived fuels in any ratio. For example, at least 5%, preferably at least 25%, more preferably at least 50%, and most preferably at least 95% by weight of the oil, may be derived from a plant or animal source.

Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1 octenes), poly(1-decenes)); alkylbenzenes (e.g., dodecylbenzenes, tetradecylbenzenes, dinonylbenzenes, di(2-ethylhexyl)benzenes); polyphenyls (e.g., biphenyls, terphenyls, alkylated polyphenols); and alkylated diphenyl ethers and alkylated diphenyl sulfides and derivative, analogs, and homologs thereof. Also useful are synthetic oils derived from a gas to liquid process from Fischer-Tropsch synthesized hydrocarbons, which are commonly referred to as gas to liquid or "GTL" base oils.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide and the alkyl and aryl ethers of polyoxyalkylene polymers (e.g., methylpolyisopropylene glycol ether having a molecular weight of 1000 or diphenyl ether of polyethylene glycol having a molecular weight of 1000 to 1500), and mono- and polycarboxylic esters thereof, for example, the acetic acid esters, mixed $C_3$-$C_8$ fatty acid esters, and $C_{13}$ oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of such esters includes dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2 ethylhexanoic acid.

Esters useful as synthetic oils also include those made from $C_5$ to $C_{12}$ monocarboxylic acids and polyols and polyol esters such as neopentyl glycol, trimethylolpropane, pentaerythritol, dipentaerythritol and tripentaerythritol.

Silicon-based oils such as the polyalkyl-, polyaryl-, polyalkoxy- or polyaryloxysilicone oils and silicate oils comprise another useful class of synthetic lubricants; such oils include tetraethyl silicate, tetraisopropyl silicate, tetra-(2-ethylhexyl) silicate, tetra-(4-methyl-2-ethylhexyl)silicate, tetra-(p-tert-butyl-phenyl) silicate, hexa-(4-methyl-2-ethylhexyl)disiloxane, poly(methyl)siloxanes and poly(methylphenyl) siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

The oil of lubricating viscosity can comprise a Group I, Group II, or Group III base stock or base oil blends of the aforementioned base stocks. Preferably, the oil of lubricating viscosity is a Group II or Group III base stock, or a mixture thereof, or a mixture of a Group I base stock and one or more of a Group II and Group III. Preferably, a major amount of the oil of lubricating viscosity is a Group II, Group III, Group IV, or Group V base stock, or a mixture thereof. The base stock, or base stock blend, preferably has a saturate content of at least 65%, more preferably at least 75%, such as at least 85%. Most preferably, the base stock, or base stock blend, has a saturate content of greater than 90%. Preferably, the oil or oil blend will have a sulfur content of less than 1%, preferably less than 0.6%, and most preferably less than 0.4%, by weight.

Preferably the volatility of the oil or oil blend, as measured by the Noack volatility test (ASTM D5880), is less than or equal to 30%, preferably less than or equal to 25%, more preferably less than or equal to 20%, most preferably less than or equal to 16%. Preferably, the viscosity index (VI) of the oil or oil blend is at least 85, preferably at least 100, most preferably from about 105 to 140.

Definitions for the base stocks and base oils in this invention are the same as those found in the American Petroleum Institute (API) publication "Engine Oil Licensing and Certification System," Industry Services Department (14th ed., December 1996), Addendum 1, December 1998. This publication categorizes base stocks as follows.

(a) Group I base stocks contain less than 90 percent saturates and/or greater than 0.03 percent sulfur and have a viscosity index greater than or equal to 80 and less than 120 using the test methods specified in Table 1.

(b) Group II base stocks contain greater than or equal to 90 percent saturates and less than or equal to 0.03 percent sulfur and have a viscosity index greater than or equal to 80 and less than 120 using the test methods specified in Table 1.

(c) Group III base stocks contain greater than or equal to 90 percent saturates and less than or equal to 0.03 percent sulfur and have a viscosity index greater than or equal to 120 using the test methods specified in Table 1.

(d) Group IV base stocks are polyalphaolefins (PAO).

(e) Group V base stocks include all other base stocks not included in Groups I, II, III, or IV.

TABLE 1

Analytical Methods for Base Stock Property Test Method

| | |
|---|---|
| Saturates | ASTM D 2007 |
| Viscosity Index | ASTM D 2270 |
| Sulfur | ASTM D 2622 |
| | ASTM D 4294 |
| | ASTM D 4927 |
| | ASTM D 3120 |

Additional additives may be incorporated in the compositions of the invention to enable them to meet particular requirements. Examples of additives that may be included in the lubricating oil compositions are dispersants, detergents, metal rust inhibitors, viscosity index improvers, corrosion inhibitors, oxidation inhibitors, friction modifiers, other dispersants, anti-foaming agents, anti-wear agents and pour point depressants. Some are discussed in further detail below.

Lubricating oil compositions of the present invention can further contain one or more ashless dispersants, which effectively reduce formation of deposits upon use in gasoline and diesel engines, when added to lubricating oils. Ashless dispersants useful in the compositions of the present invention comprise an oil soluble polymeric long chain backbone having functional groups capable of associating with particles to be dispersed. Typically, such dispersants comprise amine, alcohol, amide or ester polar moieties attached to the polymer backbone, often via a bridging group. The ashless dispersant can be, for example, selected from oil soluble salts, esters, amino-esters, amides, imides, and oxazolines of long chain hydrocarbon-substituted mono- and polycarboxylic acids or anhydrides thereof; thiocarboxylate derivatives of long chain hydrocarbons; long chain aliphatic hydrocarbons having polyamine moieties attached directly thereto; and Mannich condensation products formed by condensing a long chain substituted phenol with formaldehyde and polyalkylene polyamine.

Preferred dispersants include polyamine-derivatized poly alpha-olefin, dispersants, particularly ethylene/butene alpha-olefin and polyisobutylene-based dispersants. Particularly preferred are ashless dispersants derived from polyisobutylene substituted with succinic anhydride groups and reacted with polyethylene amines, e.g., polyisobutylene succinimide, polyethylene diamine, tetraethylene pentamine; or a polyoxyalkylene polyamine, e.g., polyoxypropylene diamine, trimethylolaminomethane; a hydroxy compound, e.g., pentaerythritol; and combinations thereof. One particularly preferred dispersant combination is a combination of (A) polyisobutylene substituted with succinic anhydride groups and reacted with (B) a hydroxy compound, e.g., pentaerythritol; (C) a polyoxyalkylene polyamine, e.g., polyoxypropylene diamine, or (D) a polyalkylene diamine, e.g., polyethylene diamine and tetraethylene pentamine using about 0.3 to about 2 moles of (B), (C) and/or (D) per mole of (A). Another preferred dispersant combination comprises a combination of (A) polyisobutenyl succinic anhydride with (B) a polyalkylene polyamine, e.g., tetraethylene pentamine, and (C) a polyhydric alcohol or polyhydroxy-substituted aliphatic primary amine, e.g., pentaerythritol or trismethylolaminomethane, as described in U.S. Pat. No. 3,632,511.

Another class of ashless dispersants comprises Mannich base condensation products. Generally, these products are prepared by condensing about one mole of an alkyl-substituted mono- or polyhydroxy benzene with about 1 to 2.5 moles of carbonyl compound(s) (e.g., formaldehyde and paraformaldehyde) and about 0.5 to 2 moles of polyalkylene polyamine, as disclosed, for example, in U.S. Pat. No. 3,442,808. Such Mannich base condensation products can include a polymer product of a metallocene catalyzed polymerization as a substituent on the benzene group, or can be reacted with a compound containing such a polymer substituted on a succinic anhydride in a manner similar to that described in U.S. Pat. No. 3,442,808. Examples of functionalized and/or derivatized olefin polymers synthesized using metallocene catalyst systems are described in the publications identified supra.

The dispersant can be further post treated by a variety of conventional post treatments such as boration, as generally taught in U.S. Pat. Nos. 3,087,936 and 3,254,025. Boration of the dispersant is readily accomplished by treating an acyl nitrogen-containing dispersant with a boron compound, such as boron oxide, boron halide boron acids, and esters of boron acids, in an amount sufficient to provide from about 0.1 to about 20 atomic proportions of boron for each mole of acylated nitrogen composition. Useful dispersants contain from about 0.05 to about 2.0 wt. %, e.g., from about 0.05 to about 0.7 wt. % boron. The boron, which appears in the product as dehydrated boric acid polymers (primarily $(HBO_2)_3$), is believed to attach to the dispersant imides and diimides as amine salts, e.g., the metaborate salt of the diimide. Boration can be performed by adding from about 0.5 to 4 wt. %, e.g., from about 1 to about 3 wt. % (based on the mass of acyl nitrogen compound) of a boron compound, preferably boric acid, usually as a slurry, to the acyl nitrogen compound and heating with stirring at from about 135° C. to about 190° C., e.g., 140° C. to 170° C., for from about one to about five hours, followed by nitrogen stripping. Alternatively, the boron treatment can be conducted by adding boric acid to a hot reaction mixture of the dicarboxylic acid material and amine, while removing water. Other post reaction processes commonly known in the art can also be applied.

The dispersant can also be further post treated by reaction with a so-called "capping agent." Conventionally, nitrogen-containing dispersants have been "capped" to reduce the adverse effect such dispersants have on the fluoroelastomer engine seals. Numerous capping agents and methods are known. Of the known "capping agents," those that convert basic dispersant amino groups to non-basic moieties (e.g., amido or imido groups) are most suitable. The reaction of a nitrogen-containing dispersant and alkyl acetoacetate (e.g., ethyl acetoacetate (EAA)) is described, for example, in U.S. Pat. Nos. 4,839,071, 4,839,072, and 4,579,675. The reaction of a nitrogen-containing dispersant and formic acid is described, for example, in U.S. Pat. No. 3,185,704. The reaction product of a nitrogen-containing dispersant and other suitable capping agents are described in U.S. Pat. No. 4,663,064 (glycolic acid); U.S. Pat. Nos. 4,612,132, 5,334,321, 5,356,552, 5,716,912, 5,849,676, and 5,861,363 (alkyl and alkylene carbonates, e.g., ethylene carbonate); U.S. Pat. No. 5,328,622 (mono-epoxide); U.S. Pat. No. 5,026,495; U.S. Pat. Nos. 5,085,788, 5,259,906, 5,407,591 (poly (e.g., bis)-epoxides); and U.S. Pat. No. 4,686,054 (maleic anhydride or succinic anhydride). The foregoing list is not exhaustive, and other methods of capping nitrogen-containing dispersants are known to those skilled in the art.

For adequate piston deposit control, a nitrogen-containing dispersant can be added in an amount providing the lubricating oil composition with from about 0.03 wt. % to about 0.15 wt. %, preferably from about 0.07 to about 0.12 wt. %, of nitrogen.

Metal-containing or ash-forming detergents function both as detergents to reduce or remove deposits and as acid neutralizers or rust inhibitors, thereby reducing wear and corrosion and extending engine life. Detergents generally comprise a polar head with a long hydrophobic tail, with the polar head comprising a metal salt of an acidic organic compound. The salts can contain a substantially stoichiometric amount of the metal, in which case they are usually described as normal or neutral salts, and would typically have a total base number or TBN (as can be measured by ASTM D2896) of from 0 to 80. A large amount of a metal base can be incorporated by reacting excess metal compound (e.g., an oxide or hydroxide) with an acidic gas (e.g., carbon dioxide). The resulting overbased detergent comprises neutralized detergent as the outer layer of a metal base (e.g. carbonate) micelle. Such overbased detergents can have a TBN of 150 or greater and typically will have a TBN of from 250 to 450 or more.

Detergents that can be used include oil-soluble neutral and overbased sulfonates, phenates, sulfurized phenates, thiophosphonates, salicylates, naphthenates, and other oil-soluble carboxylates of a metal, particularly the alkali or alkaline earth metals, e.g., sodium, potassium, lithium, calcium, and magnesium. The most commonly used metals are calcium and magnesium, which can both be present in detergents used in a lubricant, and mixtures of calcium and/or magnesium with sodium. Particularly convenient metal detergents are neutral and overbased calcium sulfonates having TBN of from 20 to 450 TBN, and neutral and overbased calcium phenates and sulfurized phenates having TBN of from 50 to 450. Combinations of detergents, whether overbased or neutral or both, can be used.

Sulfonates can be prepared from sulfonic acids which are typically obtained by the sulfonation of alkyl substituted aromatic hydrocarbons such as those obtained from the fractionation of petroleum or by the alkylation of aromatic hydrocarbons. Examples included those obtained by alkylating benzene, toluene, xylene, naphthalene, diphenyl, or their halogen derivatives such as chlorobenzene, chlorotoluene and chloronaphthalene. The alkylation can be performed in the presence of a catalyst with alkylating agents having from about 3 to more than 70 carbon atoms. The alkaryl sulfonates usually contain from about 9 to about 80 or more carbon atoms, preferably from about 16 to about 60 carbon atoms, per alkyl substituted aromatic moiety.

The oil soluble sulfonates or alkaryl sulfonic acids can be neutralized with oxides, hydroxides, alkoxides, carbonates, carboxylate, sulfides, hydrosulfides, nitrates, borates, and ethers of the metal. The amount of metal compound is chosen having regard to the desired TBN of the final product but typically ranges from about 100 to 220 wt. % (preferably at least 125 wt. %) of that stoichiometrically required.

Metal salts of phenols and sulfurized phenols are prepared by reaction with an appropriate metal compound such as an oxide or hydroxide, and neutral or overbased products can be obtained by methods well known in the art. Sulfurized phenols can be prepared by reacting a phenol with sulfur or a sulfur containing compound such as hydrogen sulfide, sulfur monohalide, or sulfur dihalide, to form products which are generally mixtures of compounds in which two or more phenols are bridged by sulfur containing bridges.

Dihydrocarbyl dithiophosphate metal salts are frequently used as antiwear and antioxidant agents. The metal can be an alkali or alkaline earth metal, or aluminum, lead, tin, molybdenum, manganese, nickel or copper. The zinc salts are most commonly used in lubricating oil in amounts of 0.1 to 10 wt. %, preferably 0.2 to 2 wt. %, based upon the total weight of the lubricating oil composition. They can be prepared in accordance with known techniques by first forming a dihydrocarbyl dithiophosphoric acid (DDPA), usually by reaction of one or more alcohols or a phenol with $P_2S_5$ and then neutralizing the formed DDPA with a zinc compound. For example, a dithiophosphoric acid can be made by reacting mixtures of primary and secondary alcohols. Alternatively, multiple dithiophosphoric acids can be prepared where the hydrocarbyl groups on one are entirely secondary in character and the hydrocarbyl groups on the others are entirely primary in character. To make the zinc salt, any basic or neutral zinc compound could be used, but the oxides, hydroxides, and carbonates are most generally employed. Commercial additives frequently contain an excess of zinc due to the use of an excess of the basic zinc compound in the neutralization reaction.

The preferred zinc dihydrocarbyl dithiophosphates are oil soluble salts of dihydrocarbyl dithiophosphoric acids and can comprise zinc dialkyl dithiophosphates. The present invention can be particularly useful when used with passenger car diesel engine lubricant compositions containing phosphorus levels of from about 0.02 to about 0.12 wt. %, such as from about 0.03 to about 0.10 wt. %, or from about 0.05 to about 0.08 wt. %, based on the total mass of the composition and heavy duty diesel engine lubricant compositions containing phosphorus levels of from about 0.02 to about 0.16 wt. %, such as from about 0.05 to about 0.14 wt. %, or from about 0.08 to about 0.12 wt. %, based on the total mass of the composition. In one preferred embodiment, lubricating oil compositions of the present invention contain zinc dialkyl dithiophosphate derived predominantly (e.g., over 50 mol. %, such as over 60 mol. %) from secondary alcohols.

The following are exemplary of such antiwear additives and are commercially available from The Lubrizol Corporation: Lubrizol 677A, Lubrizol 1095, Lubrizol 1097, Lubrizol 1360, Lubrizol 1395, Lubrizol 5139, and Lubrizol 5604, among others; and from Ciba-Geigy: Irgalube 353.

Oxidation inhibitors or antioxidants reduce the tendency of mineral oils to deteriorate in service. Oxidative deterioration can be evidenced by sludge in the lubricant, varnish-like deposits on the metal surfaces, and by viscosity growth. Such oxidation inhibitors include hindered phenols, alkaline earth metal salts of alkylphenolthioesters having preferably $C_5$ to $C_{12}$ alkyl side chains, calcium nonylphenol sulfide, oil soluble phenates and sulfurized phenates, phosphosulfurized or sulfurized hydrocarbons, phosphorous esters, metal thiocarbamates, oil soluble copper compounds as described in U.S. Pat. No. 4,867,890, and molybdenum-containing compounds.

Typical oil soluble aromatic amines having at least two aromatic groups attached directly to one amine nitrogen contain from 6 to 16 carbon atoms. The amines can contain more than two aromatic groups. Compounds having a total of at least three aromatic groups, in which two aromatic groups are linked by a covalent bond or by an atom or group (e.g., an oxygen or sulfur atom, or a —CO—, —$SO_2$— or alkylene group) and two are directly attached to one amine nitrogen, are also considered aromatic amines having at least two aromatic groups attached directly to the nitrogen. The aromatic rings are typically substituted by one or more substituents selected from alkyl, cycloalkyl, alkoxy, aryloxy, acyl, acylamino, hydroxy, and nitro groups.

Multiple antioxidants are commonly employed in combination. In one preferred embodiment, lubricating oil compositions of the present invention, in addition to the benzenediamine compound(s) added to ameliorate soot-induced viscosity increase, contain from about 0.1 to about 1.2 wt. % of aminic antioxidant and from about 0.1 to about 3 wt. % of phenolic antioxidant. In another preferred embodiment, lubricating oil compositions of the present invention contain from about 0.1 to about 1.2 wt. % of aminic antioxidant, from about 0.1 to about 3 wt. % of phenolic antioxidant and a molybdenum compound in an amount providing the lubricating oil composition from about 10 to about 1000 ppm of molybdenum. Preferably, lubricating oil compositions useful in the practice of the present invention, particularly lubricating oil compositions useful in the practice of the present invention that are required to contain no greater than 1200 ppm of phosphorus, contain ashless antioxidants other than benzenediamines, in an amount of from about 0.1 to about 5 wt. %, preferably from about 0.3 wt. % to about 4 wt. %, more preferably from about 0.5 wt. % to about 3 wt. %. Where the phosphorus content is required to be lower, the amount of ashless antioxidant other than benzenediamine will preferably increase accordingly.

The following are exemplary of the secondary diarylamine antioxidants and are commercially available from Chemtura Corporation: Naugalube™ 438, Naugalube 438L, Naugalube 640, Naugalube 635, Naugalube 680, Naugalube AMS, Naugalube APAN, Naugard PANA, Naugalube 403, Naugalube 410, and Naugalube 420; and from Ciba-Geigy: Irganox™ L 06 and Irganox L 57. The following are exemplary of substituted phenol antioxidants that are commercially available from Crompton Corporation: Naugard™ BHT, Antioxidant 431, and Naugalube 531; and from Ciba-Geigy: Irganox™ L 115, Irganox L 118, Irganox L 135, and Irgalube F 10A.

Representative examples of suitable viscosity modifiers are polyisobutylene, copolymers of ethylene and propylene, polymethacrylates, methacrylate copolymers, copolymers of an unsaturated dicarboxylic acid and a vinyl compound, interpolymers of styrene and acrylic esters, and partially hydrogenated copolymers of styrene/isoprene, styrenelbutadiene, and isoprene/butadiene, as well as the partially hydrogenated homopolymers of butadiene and isoprene.

A viscosity index improver dispersant functions both as a viscosity index improver and as a dispersant. Examples of viscosity index improver dispersants include reaction products of amines, for example, polyamines, with a hydrocarbyl-substituted mono- or dicarboxylic acid in which the hydrocarbyl substituent comprises a chain of sufficient length to impart viscosity index improving properties to the compounds. In general, the viscosity index improver dispersant can be, for example, a polymer of a $C_4$ to $C_{24}$ unsaturated ester of vinyl alcohol or a $C_3$ to $C_{10}$ unsaturated mono-carboxylic acid or a $C_4$ to $C_{10}$ dicarboxylic acid with an unsaturated nitrogen-containing monomer having 4 to 20 carbon atoms; a polymer of a $C_2$ to $C_{20}$ olefin with an unsaturated $C_3$ to $C_{10}$ mono- or dicarboxylic acid neutralized with an amine, hydroxyamine or an alcohol; or a polymer of ethylene with a $C_3$ to $C_{20}$ olefin further reacted either by grafting a $C_4$ to $C_{20}$ unsaturated nitrogen-containing monomer thereon or by grafting an unsaturated acid onto the polymer backbone and then reacting carboxylic acid groups of the grafted acid with an amine, hydroxy amine, or alcohol.

Friction modifiers and fuel economy agents that are compatible with the other ingredients of the final oil can also be included. Examples of such materials include glyceryl monoesters of higher fatty acids, for example, glyceryl mono-oleate; esters of long chain polycarboxylic acids with diols, for example, the butane diol ester of a dimerized unsaturated fatty acid; oxazoline compounds; and alkoxylated alkyl-substituted mono-amines, diamines and alkyl ether amines, for example, ethoxylated tallow amine and ethoxylated tallow ether amine.

Other known friction modifiers comprise oil-soluble organo-molybdenum compounds. Such organo-molybdenum friction modifiers also provide antioxidant and antiwear credits to a lubricating oil composition. Examples of such oil soluble organo-molybdenum compounds include dithiocarbamates, dithiophosphates, dithiophosphinates, xanthates, thioxanthates, sulfides, and the like, and mixtures thereof. Particularly preferred are molybdenum dithiocarbamates, dialkyldithiophosphates, alkyl xanthates, and alkylthioxanthates.

Additionally, the molybdenum compound can be an acidic molybdenum compound. These compounds will react with a basic nitrogen compound as measured by ASTM test D-664 or D-2896 titration procedure and are typically hexavalent. Included are molybdic acid, ammonium molybdate, sodium molybdate, potassium molybdate, and other alkaline metal molybdates and other molybdenum salts, e.g., hydrogen sodium molybdate, $MoOCl_4$, $MoO_2Br_2$, $Mo_2O_3Cl_6$, molybdenum trioxide or similar acidic molybdenum compounds.

Among the molybdenum compounds useful in the compositions of this invention are organo-molybdenum compounds of the formula: $Mo(ROCS_2)_4$ and $Mo(RSCS_2)_4$, wherein R is an organo group selected from the group consisting of alkyl, aryl, aralkyl, and alkoxyalkyl, generally of from 1 to 30 carbon atoms, preferably 2 to 12 carbon atoms, and most preferably alkyl of 2 to 12 carbon atoms. Especially preferred are the dialkyldithiocarbamates of molybdenum.

Another group of organo-molybdenum compounds useful in the lubricating compositions of this invention are trinuclear molybdenum compounds, especially those of the formula $MO_3S_kL_nQ_z$ and mixtures thereof wherein the L are independently selected ligands having organo groups with a sufficient number of carbon atoms to render the compound soluble or dispersible in the oil, n is from 1 to 4, k varies from 4 through 7, Q is selected from the group of neutral electron donating compounds such as water, amines, alcohols, phosphines, and ethers, and z ranges from 0 to 5 and includes non-stoichiometric values. At least 21 total carbon atoms should be present among all the ligand organo groups, such as at least 25, at least 30, or at least 35 carbon atoms.

The following are exemplary of molybdenum friction modifier additives and are commercially available from R. T. Vanderbilt Company, Inc.: Molyvan™ A, Molyvan L, Molyvan 807, Molyvan 856B, Molyvan 822, Molyvan 855, among others. The following are also exemplary of such additives and are commercially available from Asahi Denka Kogyo K.K.: SAKURA-LUBE™ 100, SAKURA-LUBE 165, SAKURA-LUBE 300, SAKURA-LUBE 310G, SAKURA-LUBE 321, SAKURA-LUBE 474, SAKURA-LUBE 600, SAKURA-LUBE 700, among others. The following are also exemplary of such friction modifier additives and are commercially available from Akzo Nobel Chemicals GmbH: Ketjen-Ox™ 77M, Ketjen-Ox 77TS, among others. Naugalube MolyFM is also exemplary of such additives and is commercially available from Chemtura Corporation.

Pour point depressants, otherwise known as lube oil flow improvers (LOFI), lower the minimum temperature at which the fluid will flow or can be poured. Such additives are well known. Typical of those additives that improve the low temperature fluidity of the fluid are $C_8$ to $C_{18}$ dialkyl fumarate/vinyl acetate copolymers, and polymethacrylates. Foam control can be provided by an antifoamant of the polysiloxane type, for example, silicone oil or polydimethyl siloxane. An example of a pour point depressant is polymethacrylate, and the like.

Some of the above-mentioned additives can provide a multiplicity of effects; thus, for example, a single additive can act as a dispersant-oxidation inhibitor. This approach is well known and need not be further elaborated herein.

Examples of corrosion inhibitors include amine complexes, benzotriazole-, tolyltriazole-, thidiazole-, and imidazole-based compounds, and the like. The following is an exemplary corrosion inhibitors and is commercially available from King Industries, Inc.: K-Corr™ 100A2.

Examples of viscosity index (V.I.) improvers include olefin copolymers, dispersant olefin copolymers, ethylene-α-olefin copolymers wherein the α-olefin may be propylene, 1-butene, or 1-pentene, or the hydrides thereof, polyisobutylenes or the hydrides thereof, styrene-diene hydrogenated copolymers, styrene-maleate anhydride copolymers, and polyalkylstyrenes, and the like.

Example of anti-foamants include polysiloxane, silicones such as dimethylsilicone and fluorosilicone, and the like. The following is an exemplary anti-foamant and is commercially available from Munzing/Ultra Additives: Foam Ban™ MS-575.

In the present invention it may be necessary to include an additive that maintains the stability of the viscosity of the blend. Thus, although polar group-containing additives achieve a suitably low viscosity in the pre-blending stage, it has been observed that some compositions increase in viscosity when stored for prolonged periods. Additives which are effective in controlling this viscosity increase include the long chain hydrocarbons functionalized by reaction with mono- or dicarboxylic acids or anhydrides which are used in the preparation of the ashless dispersants as hereinbefore disclosed.

When lubricating compositions contain one or more of the above-mentioned additives, each additive is typically blended into the base oil in an amount that enables the additive to provide its desired function. Representative effect amounts of such additives, when used in crankcase lubricants, are listed below. All the values listed are stated as weight percent active ingredient.

TABLE 2

| ADDITIVE | Wt % (Desirable) | Wt % (Preferred) |
| --- | --- | --- |
| Overbased Detergents | 0.1-15 | 0.2-9 |
| Corrosion Inhibitor | 0.0-5 | 0.0-1.5 |
| Anti-wear agents | 0.1-6 | 0.1-4 |
| Dispersants | 0.1-10 | 0.1-5 |
| Antioxidant | 0.0-5 | 0.01-3 |
| Pour Point Depressant | 0.0-5 | 0.01-1.5 |
| Antifoaming Agent | 0.0-5 | 0.001-0.15 |
| Friction Modifier | 0.0-5 | 0.0-1.5 |
| Viscosity Index Improver | 0.01-10 | 0.25-3 |
| Base stock | Balance (i.e. ~60-99.99) | Balance (i.e. ~80 to 99.99) |

Fully formulated passenger car diesel engine lubricating oil (PCDO) compositions of the present invention preferably have a sulfur content of less than about 0.4 wt. %, such as less than about 0.35 wt. %, more preferably less than about 0.03 wt. %, such as less than about 0.15 wt. %. Preferably, the Noack volatility of the fully formulated PCDO (oil of lubricating viscosity plus all additives) will be no greater than 13, such as no greater than 12, preferably no greater than 10. Fully formulated PCDOs of the present invention preferably have no greater than 1200 ppm of phosphorus, such as no greater than 1000 ppm of phosphorus, or no greater than 800 ppm of phosphorus. Fully formulated PCDOs of the present invention preferably have a sulfated ash (SASH) content of about 1.0 wt. % or less.

Fully formulated heavy duty diesel engine (HDD) lubricating oil compositions of the present invention preferably have a sulfur content of less than about 1.0 wt. %, such as less than about 0.6 wt. %, more preferably less than about 0.4 wt. %, such as less than about 0.15 wt. %. Preferably, the Noack volatility of the fully formulated HDD lubricating oil composition (oil of lubricating viscosity plus all additives) will be no greater than 20, such as no greater than 15, preferably no greater than 12. Fully formulated HDD lubricating oil compositions of the present invention preferably have no greater than 1600 ppm of phosphorus, such as no greater than 1400 ppm of phosphorus, or no greater than 1200 ppm of phosphorus. Fully formulated HDD lubricating oil compositions of the present invention preferably have a sulfated ash (SASH) content of about 1.0 wt. % or less.

It may be desirable, although not essential, to prepare one or more additive concentrates comprising additives (concentrates sometimes being referred to as additive packages) whereby several additives can be added simultaneously to the oil to form the lubricating oil composition. A concentrate for the preparation of a lubricating oil composition of the present invention can, for example, contain from about 0.1 to about 16 wt. % of alkylated-1,3-benzenediamine of the present invention; about 10 to about 40 wt. % of a nitrogen-containing dispersant; about 2 to about 20 wt. % of an aminic antioxidant and/or a phenolic antioxidant, a molybdenum compound, or a mixture thereof; about 5 to 40 wt. % of a detergent; and from about 2 to about 20 wt. % of a metal dihydrocarbyl dithiophosphate.

The final composition can employ from 5 to 25 wt. %, preferably 5 to 18 wt. %, typically 10 to 15 wt. %, of the concentrate, the remainder being oil of lubricating viscosity and viscosity modifier.

All weight percents expressed herein (unless otherwise indicated) are based on active ingredient (A.I.) content of the additive, and/or upon the total weight of any additive-package, or formulation which will be the sum of the A.I. weight of each additive plus the weight of total oil or diluent.

In addition to lubricants, alkylated-1,3-benzenediamines of the present invention may be used with electronic chemicals, urethanes, crop protection, pharmaceuticals, dyes and toners.

EXAMPLES

Example 1

Reductive Alkylation of 1,3-Benzenediamine with cyclohexanone

A 2000 mL bottom-out reaction kettle flask was fitted with an overhead stirrer, a thermocouple, and a nitrogen inlet. The flask was charged with 40.1 g 1,3-benzenediamine, 800 mL tetrahydrofuran, 400 mL xylenes, 96 mL cyclohexanone, and 21 mL glacial acetic acid. Sodium triacetoxyborohydride, 160.0 g, was added over 3.5 hours, as the reaction was heated from 38° C. to 65° C. The reaction was stirred at 65° C. for 2 h. The reaction was extracted with 320 g 25% aqueous sodium hydroxide, and washed three times with water. Solvent was removed by rotary evaporation to yield 96.4 g dark solid, which was recrystallized from isopropanol to give light brown crystals, mp 84-86° C. The product crystals contained $N^1,N^3$-dicyclohexyl-1,3-benzenediamine.

$^1$H NMR: δ 7.93 t, J=7.8 Hz (1H), 6.95 dd, $J_1$=7.8 Hz, $J_2$=2.3 Hz, (2H), 5.58 t, J=2.2 Hz (1H), 3.42 br s (2H, exchangeable with $CD_3OD$), 3.20 m, (2H), 2.1-1.1 (20H).

$^{13}$C NMR: δ 148.86, 130.24, 103.03, 128.704, 51.92, 33.92, 26.27, 25.35.

Example 2

Catalytic Hydrogenation of 1,3-Benzenediamine with cyclohexanone

A 1 L stainless steel autoclave was charged with 108.1 g 1,3-benzenediamine, 294.0 g cyclohexanone, and 2.0 g wet (as received) sulfided platinum on carbon catalyst. The autoclave was pressurized with 4,233 KPa (600 psig) of hydrogen. The reaction was heated to 160° C. for 4 hours. The reaction mass was cooled, yielding 272 g of a thick gray slurry, containing crude $N^1,N^3$-dicyclohexyl-1,3-benzenediamine, which was reacted further without purification.

Example 3

Catalytic Hydrogenation of 1,3-Benzenediamine with Methylisobutylketone

A 1 L stainless steel autoclave was charged with 108.1 g 1,3-benzenediamine, 300.6 g methylisobutylketone (MIBK), toluene, and 2.0 g wet (as received) sulfided platinum on carbon catalyst. The autoclave was pressurized with 4,578 KPa (650 psig) of hydrogen. The reaction was heated to 160° C. for 9 hours. The reaction mass was cooled, diluted with toluene, and filtered. Solvent was removed by rotary evaporation, yielding 242.2 g of a reddish-brown liquid, containing 78% crude $N^1,N^3$-(1,3-dimethylbutyl)-1,3-benzenediamine. The crude material was purified by vacuum distillation prior to use.

Example 4

Catalytic Hydrogenation of $N^1,N^3$-dicyclohexyl-1,3-benzenediamine produced by Example 1

A 1 L stainless steel autoclave was charged with 263.0 g of $N^1,N^3$-dicyclohexyl-1,3-benzenediamine reaction mixture prepared as described in Example 1, 59.5 g butyraldehyde, and an additional 2.0 g wet (as received) sulfided platinum on carbon catalyst. The autoclave was pressurized with 4,647 KPa (660 psig) of hydrogen. The reaction was heated to 180° C. over 4 hours, and held at 180° C. for 17 hours. The $N^1,N^3$-dicyclohexyl-4,6-dibutyl-1,3-benzenediamine has the characteristics reported below.

$^1$H NMR: δ 6.68 s (1H), 6.04 s (1H), 3.30 br (2H, exchangeable with CD3OD), 3.28 m (2H; occurs at 3.12 with added CD3OD), 2.36 t, J=7.7 Hz (4H), 2.10 m (4H) 1.8-1.2 (24H), 0.96 t, J=7.2 Hz (6H).

$^{13}$C NMR: δ 144.0, 130.6, 115.2, 96.3, 52.4, 34.1, 31.9, 30.5, 26.4, 25.3, 23.1, 14.4.

Example 5

Catalytic Hydrogenation of $N^1,N^3$-dicyclohexyl-1,3-benzenediamine produced by Example 2

To 272 g of $N^1,N^3$-dicyclohexyl-1,3-benzenediamine prepared as described in Example 2 were added 151.4 g isobutyraldehyde, and 2.0 g wet (as received) sulfided platinum on carbon catalyst. The autoclave was pressurized with 4,578 KPa (650 psig) of hydrogen. The reaction was heated to 180° C. for 5 hours. The reaction mass was cooled and filtered. The resulting liquid was separated, and the aqueous phase was discarded. Volatiles were removed from the organic phase to yield 361 g of a viscous brown liquid, which solidified on standing.

Recrystallization from ethyl acetate provided an off-white product, mp 92-94° C., containing 42% of $N^1,N^3$-dicyclohexyl-4,6-diisobutyl-1,3-benzenediamine, along with 35% $N^1,N^3$-dicyclohexyl-4-isobutenyl-6-isobutyl-1,3-benzenediamine, as determined by GC/MS.

The $N^1,N^3$-dicyclohexyl-4,6-diisobutyl-1,3-benzenediamine was further purified by treatment with bromine in tetrahydrofuran. After workup with aqueous sodium thiosulfate, the product was taken up in hexanes. The product was obtained by chromatography on silica gel with 19:1 hexanes/ethyl acetate.

$^1$H NMR: δ 6.58 s (1H), 6.02 s (1H), 3.30 br (2H, exchangeable with CD$_3$OD), 3.30 m (2H; occurs at 3.15 with added CD$_3$OD), 2.22 d, J=7.2 Hz (4H), 2.1-1.2 (22H), 0.91 d, J=6.6 Hz (12H).

$^{13}$C NMR: δ144.0, 133.5, 114.1, 96.3, 52.4, 40.7, 34.1, 28.6, 27.5, 25.3, 23.1.

IR 3420 cm$^{-1}$ w-m, (N—H).

Example 6

Catalytic Hydrogenation of $N^1,N^3$-dicyclohexyl-1,3-benzenediamine produced by Example 2

To 263.1 g of $N^1,N^3$-dicyclohexyl-1,3-benzenediamine prepared as described in Example 2 were added 59.5 g butyraldehyde, and 2.0 g wet (as received) sulfided platinum on carbon catalyst. The autoclave was pressurized with 4,647 KPa (660 psig) of hydrogen. The reaction was heated to 180° C. over 4 hours, and held at for 180° C. 17 hours. The reaction mass was cooled and filtered, and volatiles were removed by rotary evaporation. The reaction mass was contained and the $N^1,N^3$-dicyclohexyl-4-butyl-1,3-benzenediamine was isolated by column chromatography as an oil, 93.5% pure by GCMS analysis. It has the characteristics reported below.

$^1$H NMR: δ 6.80 d, J=7.8 Hz (1H), 5.93 m, (2H), 3.62 br s (2H), 3.21 m, (2H), 2.33 t, J=7.7 Hz (2H), 2.05 m, (4H), 1.8-1.1 (20H), 0.932 t, J=7.2 Hz, (3H).

IR: 3428 cm$^{-1}$ m, sharp, (N—H).

Example 7

Catalytic Hydrogenation of $N^1,N^3$-(1,3-dimethylbutyl)-1,3-benzenediamine produced by Example 3

A 1 L stainless steel autoclave was charged with 68.1 g of $N^1,N^3$-(1,3-dimethylbutyl)-1,3-benzenediamine reaction mixture prepared as described in Example 3, 54.0 g isobutyraldehyde, 300 mL of toluene and an additional 2.0 g wet (as received) sulfided platinum on carbon catalyst. The autoclave was pressurized with 4,578 KPa (650 psig) of hydrogen. The reaction was heated to 180° C. over 4 hours, and held at for 180° C. 17 hours. The reaction mass was cooled and filtered, and volatiles were removed by rotary evaporation. The liquid product mixture contained 74% of the desired $N^1,N^3$-(1,3-dimethylbutyl)-4,6-diisobutyl-1,3-benzenediamine. The next most abundant component was present at 6% (GC). This $N^1,N^3$-(1,3-dimethylbutyl)-4,6-diisobutyl-1,3-benzenediamine compound has the characteristics reported below.

$^1$H NMR: δ 6.58 s (1H), 5.99 s (1H), 6.00 s (1H), 3.55 m (2H), 3.15 br (2H, exchangeable with CD$_3$OD), 2.21 d, J=7.2 Hz (4H), 1.78 m (4H), 1.54 m (2H), 1.26 m (2H), 1.18 d, J=6.0 Hz (6H), 0.96 d, J=6.0 Hz (6H), 0.92 d, J=6.0 Hz (12H).

IR: 3434 cm$^{-1}$ m, sharp, (N—H).

Example 8

Catalytic Hydrogenation of $N^1,N^3$-(1,3-dimethylbutyl)-1,3-benzenediamine produced by Example 3

A 1 L stainless steel autoclave was charged with 68.1 g of $N^1,N^3$-(1,3-dimethylbutyl)-1,3-benzenediamine reaction mixture prepared as described in Example 3, 54.0 g butyraldehyde, 300 mL of toluene and an additional 2.0 g wet (as received) sulfided platinum on carbon catalyst. The autoclave was pressurized with 4,578 KPa (650 psig) of hydrogen. The reaction was heated to 180° C. over 4 hours, and held at for 180° C. 14 hours. The reaction mass was cooled and filtered, and volatiles were removed by rotary evaporation. The liquid product mixture contained 72% of the desired $N^1,N^3$-(1,3-dimethylbutyl)-4,6-dibutyl-1,3-benzenediamine. The next most abundant component was present at 6% (GC). This $N^1,N^3$-(1,3-dimethylbutyl)-4,6-dibutyl-1,3-benzenediamine compound has the characteristics reported below.

$^1$H NMR: δ 6.68 s (1H), 6.00 s (1H), 3.72 m (2H), 3.35 br (2H, exchangeable with CD$_3$OD), 2.52 m (4H), 1.94 m (2H), 1.72 m (4H), 1.58 m (4H), 1.47 m (2H), 1.36 d, J=6.3 Hz (6H), 1.13 m, (18H).

IR: 3435 cm$^{-1}$ m, (N—H).

Example 9

Catalytic Hydrogenation of N,N'-dicyclohexyl-1,3-benzenediamine produced by Example 2 with benzaldehyde A 1 L stainless steel autoclave was charged with 65.0 g of $N^1,N^3$-dicyclohexyl-1,3-benzenediamine reaction mixture prepared as described in Example 2, 79.5 g benzaldehyde, 300 mL of toluene and an additional 2.0 g wet (as received) sulfided platinum on carbon catalyst. The autoclave was pressurized with 4,578 KPa (650 psig) of hydrogen. The reaction was heated to 180° C. over 4 hours, and held at for 180° C. 4 hours. The reaction was cooled and filtered, and volatiles were removed by rotary evaporation. The product was recrystallized from 4:1 hexanes/ethyl acetate to yield beige crystals, mp 152-154° C. This $N^1,N^3$-dicyclohexyl-4,6-dibenzyl-1,3-benzenediamine compound has the characteristics reported below.

$^1$H NMR: δ 7.25 m (10H), 6.78 s (1H), 6.00 s (1H), 3.80 s (4H), 3.3 br s (2H, exchangeable with CD$_3$OD), 3.17 m (2H), 1.8-1.0 (20H).

$^{13}$C NMR: δ 145.39, 141.16, 128.74, 128.73, 126.30, 113.22, 96.21, 51.83, 38.06, 33.40, 26.25, 24.8.

IR: 3424 cm$^{-1}$ s, sharp, (N—H).

Example 10

Catalytic Hydrogenation of $N^1,N^3$-(1,3-dimethylbutyl)-1,3-benzenediamine produced by Example 3 with benzaldehyde A 1 L stainless steel autoclave was charged with 69.0 g of $N^1,N^3$-(1,3-dimethylbutyl)-1,3-benzenediamine reaction mixture prepared as described in Example 3, 79.5 g benzaldehyde, 300 mL of toluene and an additional 2.0 g wet (as received) sulfided platinum on carbon catalyst. The autoclave was pressurized with 4,578 KPa (650 psig) of hydrogen. The reaction was heated to 180° C. over 0.6 hours, and held at for 180° C. 6 hours. The reaction was cooled and filtered, and volatiles were removed by rotary evaporation. The product was recrystallized from isopropanol to yield tan crystals m.p. 130-132° C. This $N^1,N^3$-(1,3-dimethylbutyl)-4,6-dibenzyl-1,3-benzenediamine compound has the characteristics reported below.

$^1$H NMR: δ 7.12 m (10H), 6.77 s (1H), 5.98 s (1H), 3.79 s (4H), 3.40 m (2H; occurs at 3.15 with added CD$_3$OD), 3.15 br (2H, exchangeable with CD$_3$OD), 1.4-0.6 (10H), 1.0 d, J=6.0 Hz (6H), 0.82 d, J=6.3 Hz (6H), 0.79 d, J=6.3 Hz (6H).

$^{13}$C NMR: δ 145.7, 141.2, 134.0, 128.72, 128.71, 126.3, 112.8, 95.3, 47.1, 46.6, 38.0, 25.1, 23.2, 22.9, 21.5.

IR: 3419 cm$^{-1}$ m, (N—H).

Comparative Example A

A 100 mL 3-neck flask was fitted with an overhead stirrer, a thermocouple, and a nitrogen inlet. The flask was charged with 2.10 g of $N^1,N^3$-dicyclohexyl-1,3-benzenediamine prepared as described in Example 1, 18 mL tetrahydrofuran, 9 mL xylenes, and 1.4 mL isobutyraldehyde. The mixture was heated to 52° C. and sodium triacetoxyborohydride, 2.06 g, was added over 1.3 hours, and the reaction was stirred for 30 minutes. The reaction was warmed to 70° C., and an additional 1.39 sodium triacetoxyborohydride was added. The reaction was stirred at 70° C. for 1 h. An additional 0.7 mL isobutylaldehyde and 1.04 g sodium triacetoxyborohydride, were added, and the reaction was stirred for 0.7 h. The reaction was taken up in xylenes, extracted with aqueous sodium hydroxide, and washed twice with water. Solvent was removed by rotary evaporation to yield 2.70 g dark brownish orange oil. The oil was chromatograph on alumina with hexanes.

$^1$H NMR: δ 7.03 m (1H), 6.244 s (1H), 6.240 d, J=6.6 Hz (2H), 3.38 m (2H), 2.88 d, J=6 Hz (4H), 1.94 apparent septet, J=6.9 Hz (2H) 1.8-1.1 (20H), 0.90 d, J=6.6 Hz, (12H).

$^{13}$C NMR: δ 150.78, 129.00, 106.05, 104.11, 60.97, 52.79, 31.44, 26.91, 26.77, 26.35, 21.06.

IR: N—H absent at 3400 cm$^{-1}$.

In comparison to Examples 4 and 5, Comparative Example A, ($N^1,N^3$-dicyclohexyl-$N^1,N^3$-diisobutyl-1,3-benzenediamine) converted the secondary amines to tertiary amines. There was no alkylation of the benzene in Comparative Example A.

Comparative Example B

A 250 mL 3-neck flask was fitted with an overhead stirrer, a thermocouple, and a nitrogen inlet. The flask was charged with 4.20 g of $N^1,N^3$-dicyclohexyl-1,3-benzenediamine prepared as described in Example 1, 26 mL tetrahydrofuran, 13 mL xylenes, and 5.62 g sodium triacetoxyborohydride. The reaction was heated to 40° C. and 2.4 mL heptaldehyde was added over 40 minutes. The reaction was stirred for an additional 70 minutes. An additional 0.4 mL heptaldehyde was added, and the reaction was stirred for 80 minutes. The reaction was taken up in xylenes, extracted with aqueous sodium hydroxide, and washed twice with water. Solvent was removed by rotary evaporation to yield 5.60 g brownish orange oil. The oil was chromatograph on alumina with 98:2 hexanes/ethyl acetate.

$^1$H NMR: δ 7.03 t, J=8.1 Hz (1H), 6.08 m (3H), 3.52 m (2H), 3.10 m (4H), 1.8-1.1 (40H), 0.89 t, J=6.6 Hz (6H).

$^{13}$C NMR: 150.11, 129.73, 101.77, 97.92, 57.80, 45.79, 32.28, 31.21, 30.46, 29.58, 27.69, 26.66, 26.33, 22.92, 14.36.

IR: N—H absent at 3400 cm$^{-1}$.

In comparison to Examples 4 and 5, Comparative Example B, ($N^1,N^3$-dicyclohexyl-$N^1,N^3$-diheptyl-1,3-benzenediamine) converted the secondary amines to tertiary amines. There was no alkylation of the benzene in Comparative Example B.

Examples 11-17

Thermo-Oxidation Engine Oil Simulation Test (TEOST)

The engine oil formulation used in the tests contained the following components that are commercially available. There is no particular restriction on the type and exact composition of the materials in the context of the present invention. The exemplary test formulation is a fully formulated Group II oil omitting AO, formulated with typical commercial additives as described above. The significant reduction in deposits that results from the usage of a cycloalkyl-benzenediamine, according to the practice of this invention, has been convincingly demonstrated in an engine oil formulation by the Mid-High Temperature Thermo-oxidation Engine Oil Simulation Test (MHT-TEOST). This test is an accelerated oxidation test. The test determines the mass of a deposit formed on a specially constructed steel rod by stressing continuously a repetitive passage of 8.5 of test oil under thermal-oxidative and catalytic conditions. The instrument used was manufactured by Tannas Co. and has a typical repeatability of 0.15(x+16) mg wherein x is the mean of two or more repeated test results. The TEOST test conditions are listed in Table 4. The lower the amount of deposits obtained, the better the oxidation stability of the oil

TABLE 4

| MHT-TEOST Test Conditions | |
|---|---|
| Test Parameters | Settings |
| Test duration | 24 hours |
| Rod Temperature | 285° C. |
| Sample size | 8.5 g (mixture of 8.4 g of oil and 0.1 g of catalyst) |
| Sample flow rate | 0.25 g/min |
| Flow rate (dry air) | 10 mL/min |
| Catalyst | Oil soluble mixture containing Fe, Pb, and Sn |

The secondary diarylamine used in the test was a complex mixture of predominantly mono-, di- and tri-nonyl diphenyl amines currently sold under the trade designation Naugalube™ 438L, which is commercially available from Chemtura Corporation. Table 5 below gives the MHT-TEOST results for oils containing substituted benzenediamine of Examples 4-10.

TABLE 5

MHT-TEOST RESULTS

| Example | Secondary diaryl amine antioxidant | Wt % | Substituted benzenediamine | Wt % | (mg deposit) |
|---|---|---|---|---|---|
| 11 | Naugalube ™ 438L | 0.75 | Example 4 $N^1,N^3$-dicyclohexyl-4,6-dibutyl-1,3-benzenediamine | 0.50 | 33 |
| 12 | Naugalube ™ 438L | 0.75 | Example 5 $N^1,N^3$-dicyclohexyl-4,6-diisobutyl-1,3-benzenediamine | 0.50 | 32 |
| 13 | Naugalube ™ 438L | 0.75 | Example 6 $N^1,N^3$-dicyclohexyl-4-butyl-1,3-benzenediamine | 0.50 | 19 |
| 14 | Naugalube ™ 438L | 0.75 | Example 7 $N^1,N^3$-(1,3-dimethylbutyl)-4,6-diisobutyl-1,3-benzenediamine | 0.50 | 54 |
| 15 | Naugalube ™ 438L | 0.75 | Example 8 $N^1,N^3$-(1,3-dimethylbutyl)-4,6-dibutyl-1,3-benzenediamine | 0.50 | 56 |
| 16 | Naugalube ™ 438L | 0.75 | Example 9 $N^1,N^3$-dicyclohexyl-4,6-dibenzyl-1,3-benzenediamine | 0.50 | 36 |
| 17 | Naugalube ™ 438L | 0.75 | Example 10 $N^1,N^3$-(1,3-dimethylbutyl)-4,6-dibenzyl-1,3-benzenediamine | 0.50 | 65 |

Comparative Examples C-G

Comparative Example C contained only the 0.75% secondary amine base-treat level of antioxidant, with no cycloalkyl benzenediamine deposit control/antioxidant additive. Comparative Example D contained 1.25% of secondary amine, substituting additional secondary diphenylamine for the benzenediamine deposit control/antioxidant additive. Comparative Example E contained the 0.75% secondary amine base-treat level of antioxidant, with 0.5% Naugalube™ 531 antioxidant substituted for the cycloalkyl benzenediamine deposit control/antioxidant additive. Naugalube™ 531 antioxidant is a mixture of $C_7$-$C_9$ esters of 3,5-di-tert-butyl-hydroxycinnamic acid and is commercially available from Chemtura Corporation. Comparative Example F contained the 0.75% secondary amine base-treat level of antioxidant, with 0.5% Flexzone™ 4 L antioxidant substituted for the cycloalkyl benzenediamine deposit control/antioxidant additive. Flexzone™ 4 L antioxidant is N,N'-bis(methylpentyl)-para-benzenediamine and is commercially available from Chemtura Corporation. Comparative Example G was the exemplary test formulation run as prepared with no added antioxidant. The MHT-TEOST results are provided in Table 6 below.

TABLE 6

| Comp. Example | Secondary diaryl amine antioxidant | Wt % | (mg deposit) |
|---|---|---|---|
| C | Naugalube ™ 438L dinonyl diphenylamine | 0.75 | 72 |
| D | Naugalube ™ 438L dinonyl diphenylamine | 1.25 | 59 |
| E | Naugalube ™ 531 3,5-di-t-butyl-hydroxycinnamic acid, $C_7$-$C_9$ branched ester | 0.50 | 56 |
| F | Flexzone ™ 4L N,N'-bis(methylpentyl)-p-benzenediamine | 0.50 | 48 |
| G | No added antioxidant | 0.00 | 110 |

The deposits obtained for Inventive Examples 11-17 are significantly lower than the deposits obtained for Comparative Examples C-G. This demonstrates that the lubricating oil compositions containing appropriate mixtures of the deposit control/antioxidant blends of the present invention have superior oxidative stabilities to produce smaller amounts of deposits in the MHT-TEOST.

In view of the many changes and modifications that can be made without departing from principles underlying the present invention, reference should be made to the appended claims for an understanding of the scope of the protection to be afforded the invention.

The disclosures of all patents, articles and other materials described herein are hereby incorporated, in their entirety, into this specification by reference. Compositions described as "comprising" a plurality of defined components are to be construed as including compositions formed by admixing the defined plurality of defined components. The principles, preferred embodiments, and modes of operation of the present invention have been described in the foregoing specification. What the Applicants submit is their invention, however, is not to be construed as limited to the particular embodiments disclosed, since the disclosed embodiments are regarded as illustrative rather than limiting. Changes can be made by those skilled in the art without departing from the spirit of the invention.

What is claimed is:

1. A compound of structure (I) having the general formula:

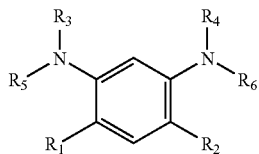
(I)

wherein $R_1$ and $R_2$ are the same and are selected from the group consisting of n-propyl, 1-methylethyl, n-butyl, isobutyl, sec-butyl, 1,3-dimethylbutyl, n-pentyl, isopentyl, hexyl, 2-methyl-propenyl, cyclopentyl, cyclohexyl, wherein $R_3$ and $R_4$ are independently selected from the group consisting of $C_1$-$C_{20}$ alkyl, 2-methyl-propenyl, benzyl, cyclopentyl, cyclohexyl, cycloheptyl and cyclooctyl; and wherein $R_5$ and $R_6$ are independently selected from the group consisting of hydrogen, $C_1$-$C_{20}$ alkyl, 2-methyl-propenyl, benzyl, cyclopentyl, cyclohexyl, cycloheptyl and cyclooctyl benzyl.

2. The compound of claim 1, wherein $R_3$ and $R_4$ are selected from the group consisting of cyclohexyl and 1,3-dimethylbutyl.

3. The compound of claim 1, wherein the compound has a structure selected from:

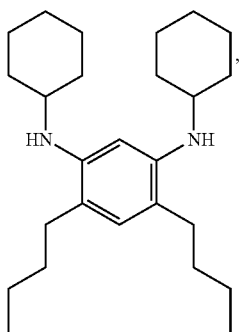
(XIII)

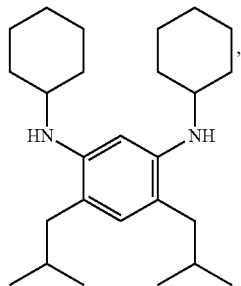
(XIV)

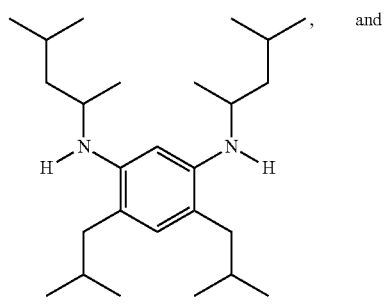
(XVIII), and

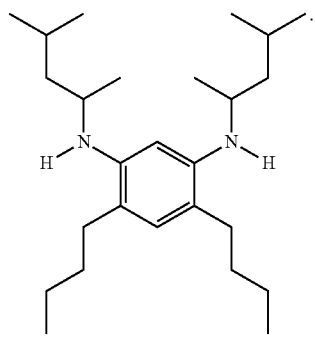
(XIX).

* * * * *